United States Patent [19]
Hasegawa et al.

[11] Patent Number: 5,380,772
[45] Date of Patent: Jan. 10, 1995

[54] MODELLING LIQUID FOR DENTAL PORCELAIN

[75] Inventors: Akira Hasegawa, Inuyama; Tsugumichi Kawasaki, Nagoya, both of Japan

[73] Assignee: G-C Toshi Kogyo Corporation, Kasugai, Japan

[21] Appl. No.: 70,010

[22] Filed: May 27, 1993

Related U.S. Application Data

[63] Continuation of Ser. No. 619,979, Nov. 30, 1990, abandoned.

[30] Foreign Application Priority Data

Dec. 11, 1989 [JP] Japan .............................. 1-318826
Sep. 28, 1990 [JP] Japan .............................. 2-257057

[51] Int. Cl.6 .............................................. C08F 2/46
[52] U.S. Cl. ........................................ 522/14; 522/24; 522/81; 522/908; 522/116; 433/202.1; 433/228.1
[58] Field of Search .................. 522/14, 21, 24, 81, 522/908; 523/116; 433/202.1, 228.1

[56] References Cited

U.S. PATENT DOCUMENTS

| | | | |
|---|---|---|---|
| 3,880,662 | 4/1975 | Daskalow et al. | 106/35 |
| 3,966,573 | 6/1976 | Bean | 522/14 |
| 4,046,732 | 9/1977 | Infante | 260/31.2 R |
| 4,347,174 | 8/1982 | Nagase et al. | 522/908 |
| 4,437,836 | 3/1984 | Schmitz-Josten et al. | 522/14 |
| 4,604,059 | 8/1986 | Klaus et al. | 433/217.1 |
| 4,674,980 | 6/1987 | Ibsen et al. | 522/14 |
| 4,820,744 | 4/1989 | Kubota et al. | 522/14 |
| 4,940,676 | 7/1990 | Evans | 501/16 |
| 5,063,257 | 11/1991 | Akahane et al. | 522/14 |

FOREIGN PATENT DOCUMENTS 0328772  8/1989  European Pat. Off. .

*Primary Examiner*—Marion E. McCamish
*Assistant Examiner*—Mark A. Chapman
*Attorney, Agent, or Firm*—Oblon, Spivak, McClelland, Maier & Neustadt

[57] ABSTRACT

A modelling liquid used for building up dental porcelain, comprising:
- (A) a photopolymerizable compound having at least one ethylenically unsaturated double bond,
- (B) a photopolymerization initiator,
- (C) a reducing agent, and
- (D) a polymerization inhibitor.

13 Claims, No Drawings

MODELLING LIQUID FOR DENTAL PORCELAIN

This application is a continuation Ser. No. 07/619,979, filed on Nov. 30, 1990, now abandoned.

BACKGROUND OF THE INVENTION

Field of the Invention

The present invention relates to a modelling liquid for dental porcelain used for preparing various prostheses partially or wholly formed of porcelain by crownwork and bridge work, while taking into account the form of teeth, their harmony with the remaining teeth, occlusion and mastication, their aesthetic appearance, their influence on periodontinum, the maintenance of recovery, their dynamic properties, their easy-to-prepare property, improvements in their quality and reliability and reductions in their production cost.

Prior Art

For crownwork and bridge work, jacket crowns, inlays and onlays have now increasingly been made of ceramics such as castable ceramics and sintered all-ceramics. In addition to techniques using castable ceramics produced by casting, refractory model and platinum foil processes have typically been well-used until now. The refractory model process involves making a denture mold of a refractory model material developed exclusively for building up and firing porcelain, building up and firing porcelain on the denture mold, removing the denture mold from the refractory model and, finally, returning the porcelain to the denture mold for form correction, and the platinum foil process comprises pressing an about 25 μm thick platinum foil on a denture mold, building up and firing all parts of porcelain including a perignathic part on the denture mold and removing the porcelain from the inner face of the crown after all dental works such as glazing are finished and before cementation. Apart from these processes, however, firing porcelain to a metallic coping or frame is also of great importance, when taking into consideration form of teeth, its harmony with remaining teeth, occlusion and mastication, its aesthetic appearance, its influence on periodontinum, maintenance of recovery, its dynamic properties and durability, etc. If crownwork or bridge work is carried out with such a metallic coping or frame, then dynamic properties of the prosthesis are improved with a reduction in the natural teeth or abutment teeth to be cut off. This also permits the prosthesis to have a good influence on the periodentinum and to be in harmony with the remaining teeth, leading to the oral cavity being in good health in its entirety. Alternatively, such aesthetic improvements may be achieved by bonding or joining porcelain to resin, especially, a hard resin. However, although the bonding or joining of porcelain to the hard resin is easily achievable within a short time and a reasonable cost, yet it has many defects, as typically set forth below:

1. the material is much inferior in wear resistance to porcelain;
2. the material absorbs much water and is so chemically instable that it is likely to be discolored or colored in the oral cavity;
3. the aesthetic appearance of the material is far from that of natural teeth; and
4. the material is poor in the adhesion to a metallic coping or frame and is lacking in durability as well.

For these reasons, there has recently been an increasing demand for prostheses having an improved aesthetic appearance, especially, a high quality. Crown work and bridge work prosthetics with porcelain fired to a metallic coping or frame have thus been heavily used in dentistry.

According to such prosthesis, a metallic coping or frame is first fitted onto a denture mold. Then, opaque, dentin and enamel porcelain materials are fundamentally build up on the denture mold in that order from its cervical periphery with the direct use of a brush or spatula. Whenever each porcelain material is built up, condensation to remove moisture and firing are carried out with the metallic coping or frame attached to the denture mold. Problems with this, however, are that because of relying upon the metallic coping or frame, the porcelain cannot completely be built up and is contracted by firing. As a result, the porcelain built up on the cervical periphery is insufficient in thickness or made thin, so that the metallic color of the coping or frame is seen through. Furthermore, the metallic coping or frame is often exposed to view through the cervical periphery in the cause of gingival recession in the oral cavity over an extended period. These are not only considerably unnatural from the aesthetic standpoint but also induce gingival discoloration or periodontitis. In order to solve such problems, use has recently been made of a margin porcelain technique in which no metallic part is provided on the shoulder region of the cervical periphery of the metallic coping or frame. With this process in which porcelain materials are built upon a region lined with no metal, it is possible to solve the problems that the color of the metallic coping or frame is seen through the porcelain materials and the metallic coping or frame is exposed to view. Required to this end, however, is some workmanship, because considerable technical difficulty is encountered in carrying out this process with conventional techniques so far available. For instance, fairly elaborate workmanship is required for condensing each porcelain material whenever it is mixed with water and, thereafter, removing the porcelain materials from the denture model of the working model without damaging their part on the region lined with no metal. To this end, various measures have been taken and various methods have been used for providing an easy separation of the porcelain materials from the denture model. The first method—called the refractory model method as already mentioned—involves building up and firing the cervical periphery on a denture model formed of a refractory material. The second method—called the platinum foil method as again mentioned above—comprises pressing a platinum foil upon the cervical periphery and building up porcelain thereon, followed by removing and firing. The third method is referred to as a making-model-hydrophobic method according to which porcelain is built up on a denture model formed of hydrophobic epoxy or a gypsum working model on which a hydrophobic release materials or surface curing materials have been coated to make it hydrophobic. The porcelain mixed with water is so poor in wetting to the hydrophobic denture model that its removal is achieved more easily than is possible with conventional gypsum working models. The 4th method comprises mixing a baking residual-free wax melt with porcelain, immediately building up the wax mixture on the shoulder and cooling and removing it from the gypsum model together with the metallic coping or frame. Usually, the wax is mixed with porcelain at a weight ratio of one to six or seven. The 5th method uses an exclusive modelling liquid curable by warm air, said modelling liquid undergoing a curing reaction by heat. The modelling liquid, not curable at room temperature, is mixed with porcelains, and the mixture is cured by warm air and then removed from a gypsum working model. The 6th method relies upon curing by exposure to visible light. On the basis of the same principle to that in the 5th method, however, this is characterized by making use of light in place of heat.

References will now be made to part of special effects of porcelain heretofore applied and having correlation with the present invention. As a matter of course, natural teeth undergo various changes depending upon age and intra-oral environments. In recent years, there has thus been an increasing demand for dental prostheses which are as fit to individual patients and close to natural teeth as possible. The special effects are a dental technique for this purpose, which is used to impart individual characteristics to each patient in consideration of color, form and region. For instance:

1. the cervical effect for reproducing the dentin of the root or the gingival color effect for achieving harmony with the gingiva;
2. the dentinal effect for reproducing insufficient calcification, structural deficiency or differences in the thickness of the dentinal core or upper enamel;
3. the incisal effect for reproducing calcification deficiency and internal stains; and
4. the surface coloration effect for reproducing stains naturally brought on teeth by tobacco, food, drinks, caries and for other reasons.

In order to attain such effects, coloration may be carried out with a porcelain material of the desired color after the building up of a basic porcelain material is nearly finished or while it is being built up. For instance, the porcelain material exclusive for internal coloration may be put into the porcelain material cut out or open along the line or points of the desired form in the course of building up or coated on the porcelain material after building up, thereby imparting individual characteristics to the teeth of each patient. Afterwards, the porcelain material may be pre-dried for 5 to 10 minutes and then baked from about 600° C. to about 900° C. at a heating rate of 50°-60° C. per minute.

Conventional techniques for building up porcelains, which are found to have some problems, are generally broken down into two cases.

First Case: without locating a metallic coping or frame at the cervical region, a porcelain is built up with the margin porcelain technique, thereby preventing their color from seeing through it; and Second Case: in order to obtain dental prostheses as close to nature teeth as possible, the special effects are imparted to them with a porcelain material for internal or external coloration.

FIRST CASE

In what follows, the problems with the respective cases will be explained.

1. The refractory model process requires to place porcelain from the gypsum working model to the refractory model and takes about three-hour longer than does the direct process, since considerable time is required for impression taking and drying and sophisticated dental work is needed. Also, an impression of inferior accuracy results in a decrease in fitting accuracy.

2. The platinum foil process, in which a platinum foil is pressed upon the cervical periphery of the gypsum working mode, is inferior in fitting accuracy due to the thickness of the platinum foil. Designed to be discarded or thrown away after use, the platinum foil gives rise to a considerable cost increase.

3. The process, in which porcelain is built up direct by a brush or a spatula with condensation, cannot be used without considerable workmanship, since the form of the cervical periphery tends to get out of shape. Nor is this process applicable to a bridging prosthesis using a plurality of abutment teeth. It is also required to allow the condensed porcelain to be easily removed from the gypsum working model by coating a hydrophobic releasing or surface curing material on its cervical periphery. In this case, however, the fitting of the porcelain to the cervical periphery gets worse relative to the thickness of the hydrophobic release or surface curing material coated.

4. With the process in which a mixture of a wax melt with porcelain is built up, cooled and removed from a gypsum working model, the wax has to be melted as many times as is necessary, because it begins to cure immediately in the course of building up due to the crystallinity of the wax being very high. Because the wax is incapable of being condensed, the porcelain contracts largely. When the wax is used in large amounts, there is produced a large amount of carbon, which contaminates, or causes a breakdown of, the furnace.

5. With the process in which porcelain is built up with a modelling liquid curable by heat, the porcelain built up, which is being cured by warm air, is softened by heat and moved by wind pressure into the metallic coping or frame, where it tends to cure. Such a porcelain should preferably be removed before or after firing. However, it is so impossible to remove this completely that the fitness of the metallic coping or frame becomes worse. This holds for the process in which a mixture of a wax melt with porcelain is built up, cooled and removed from a gypsum working model.

6. The process, in which porcelain is built up with a modelling liquid curable with light, is now commercially available. In the case of this process, however, the porcelain cannot be condensed at all. After firing, there remains in most cases carbon residues, which add a gray tone or possibly a black tone to the porcelain depending upon the firing conditions. Thus, it is not applicable at all to porcelain fired to a metal, to the aesthetic appearance of which great importance is attached.

SECOND CASE

1. In order to impart to porcelain the special effects for which complicated color tones have to be expressed, an internally or externally multi-coloring porcelain materials are generally mixed with dentin or enamel porcelain, as the occasion may demand. In that case, water has so far been used as a modelling liquid. Even though a mixture of the internally or externally coloring porcelain with water is built up and well-condensed, however, it would be impossible to make and accurate estimation of what color tone will come out after firing. This is because the refractive index (3.3327 at 23° C.) of water is largely different from that (1.47-1.50) of porcelains. Porcelains are also often colored with a dye. In that case, it is impossible to estimate the inherent color of the porcelain beforehand, unless the dye is fired. The production of such special effects, which is often practiced by the sixth sense of dental technicians, is fairly clumsy for novices and is clinically achievable only by some experts. Even when porcelains are successfully built up with the internally or externally coloring porcelain material selected, the desired color tone is not always obtained after firing. In that case, the porcelain has to be cut off to build up and fire fresh porcelain with an internally or externally coloring porcelain material of a different color tone. Thus color tone and quality of the prosthesis after being fired are deteriorated and repetition of such operations is very timeconsuming.

2. In order to express internal or external stains caused by cracking, yellowing, etc. and insufficient calcification, special-effect colors are applied to porcelain by means of a thin brush. In this case, however, the lamination of a plurality of internally coloring porcelain materials or the application of an externally coloring porcelain material gives rise to color mixing. Also, the thus drawn line is made so thick that it becomes blurred. Even when the coloring porcelain materials are built up on or applied onto a limited region, they tend to flow and spread over the porcelain. Thus, the internally or externally coloring porcelain materials cannot be used without relying upon some experts. It is neither possible to express the special effects demanded with a certain quality at any desired time.

As a result of extensive and intensive studies made to solve the above-mentioned problems, the inventors have found that they can be successfully solved by developing a modelling liquid for dental porcelain, which comprises a photopolymerizable or polymerizable compound having at least one ethylenically unsaturated double bond or an organic solvent and an organic material solid or semi-solid at normal temperature and has a refractive index of 1.4 to 1.6 inclusive at 23° C. and a viscosity of 0.1 Pa.s less at 23° C. When mixed with porcelains, this liquid can be fired to a metal and sintered without leaving behind any incineration residues, and without effecting any change to the desired color tone of porcelain at all. In what follows, how to solve the above-mentioned problems will be explained illustratively.

(In order to prevent the metallic color of the cervical periphery of a metallic coping or frame from being seen through or exposed to view, porcelains are built up with the margin porcelain technique but without applying the metallic coping or frame to the cervical periphery)

1. In order to build up porcelains direct on a non shoulder metallic coping or frame instead of using a refractory model material, the porcelain built up in any form on the cervical periphery must be maintained in the desired shape. After mixed with porcelain, the modelling liquid for dental porcelain according to this invention is built up on the cervical periphery and then exposed to light or reacts with the organic peroxide or pyrimidinetrione derivative and organometallic compound contained in the porcelain. The thus cured porcelain is temporarily bonded to the metallic coping or frame and so is easily removed from a gypsum working model, so that its shape, as built up on the cervical periphery, can be maintained to the end. Thus, troublesome dental operations such as the building up and sintering of porcelains on a refractory model can be dispensed with. Consequently, the length of time including a time for placing porcelains from the gypsum working model onto the refractory model can be much reduced with improvements in fitting accuracy.

2. Building up porcelains on a non shoulder metallic coping or frame lined with a platinum foil is troublesome and timeconsuming, fails to maintain the cervical periphery in good condition, and incurs considerable expense due to the platinum foil being costly. The modelling liquid for dental porcelain according to this invention is much cheaper than the platinum foil, say, on the order of one tenth to a few tenths or one hundredth to a few hundredths.

3. When porcelains are condensed with water for its removal, as carried out conventionally, the form of the cervical periphery is so maintained only by wet bonding that it becomes out of shape even upon receiving a slight vibration or impact. Thus this cannot be applied to a bridge work using a plurality of abutment teeth. It requires five to ten year experience to master this method. After mixed with porcelains and built up in place, the modelling liquid for dental porcelain according to this invention is cured by exposure to light or reaction with the organic peroxide or pyrimidinetrione derivative and organometallic compound contained in the porcelain. Thus, the porcelain can be so easily removed from a gypsum working model that the form of the cervical periphery can be maintained to the end. This technique makes it possible to immediately remove the porcelain built up on the cervical periphery from the gypsum working model without any craftmanship, and so is easily applicable to bridge work using a plurality of abutment teeth. When porcelains are condensed with water for its removal, as carried out conventionally, it is required that a hydrophobic release material or a surface curing agent be applied to the cervical periphery of the gypsum working model for easy removal of the condensed porcelain. Thus, the fitting of the porcelain to the cervical periphery gets worse relative to the thickness of the release material or surface curing material applied. The modelling liquid after being mixed with porcelains, and the porcelains thus mixed being built up in place, the modelling for dental porcelain according to this invention is cured by exposure to light or reaction with the organic peroxide or pyrimidinetrione derivative and organometallic compound contained in the porcelain. Thus, the porcelain can be easily removed from the gypsum working model with no need of using such a hydrophobic release material or surface curing material. Consequently, the fitting of the the cervical periphery of the porcelain fired to a metal to the gypsum working model or even to the abutment teeth of a patient is much improved.

4. In the case of the technique with wax, a wax melt is mixed with porcelains, which is then built up in place and cooled off, followed by its removal from a gypsum working model. However, the porcelain solidifies immediately after being built up, and so cannot be mixed due to the crystallization of the wax being very high. Since the wax cannot be condensed, neither is it possible to remove excessive wax by tissue papers or gauzes. Thus, the porcelain built up contracts largely after firing, and produces much carbon at the time of firing, which contaminate, or cause a breakdown of, a furnace. The modelling liquid for dental porcelain according to this invention, however, shows a viscosity sufficient for condensation after mixed with porcelain and built up in place and before exposure to light or reaction with the organic peroxide or pyrimidinetrione derivative and organometallic compound contained in the porcelain.

Thus, when the modelling liquid is in excess, such liquid can be removed by tissue papers or gauzes. According to this invention, the organic material solid or semi-solid at normal temperature—generally called the "wax" is not used as such. That organic material is diluted with an organic solvent capable of solubilizing the wax even slightly, and is then condensed with porcelain while the relative amount of the wax is reduced. After building up, the porcelain is heated to a temperature higher than the boiling point of the organic solvent to volatilize the organic solvent alone, whereby the form of the porcelain can be maintained with a small amount of the wax residue. Subsequent incineration can further improve the fired porcelain because of the small amount of the wax residue. Thus, since the amount of the photopolymerizable or polymerizable compound having at least one ethylenically unsaturated double bond, which always contains carbon, can be reduced as much as possible relative to the amount of porcelain, there is no fear that much carbon may be produced at the time of incinerating, contaminating, or causing a breakdown of a furnace.

5. In the event of the technique of building up porcelains with a modelling liquid curable by heat, the built up porcelains, while being cured by warm air, flows into a metallic coping or frame, where it cures. It is thus required that an excessive portion of the modelling liquid be removed before firing or at the end of operation. When that removal is unsuccessful, the fitting of the porcelain to a gypsum working model at the cervical periphery of a metallic coping or frame or even to the abutment teeth of a patient gets worse. With the modelling liquid for dental porcelain according to this invention, however, it is unnecessary to apply warm air, since it is cured by exposure to light or reaction with the organic peroxide or pyrimidinetrione derivative and organometallic compound contained in the porcelain. Therefore, the fitting of the porcelain to the gypsum model at the cervical periphery of the metallic coping or frame or even to the abutment teeth of a patient is much improved.

6. The technique of building up porcelains with a photo-curable modelling liquid is commercially available. Since this makes use of a polyfunctional monomer having a high viscosity, any condensation is not possible at all. After firing, there nearly always remains carbon, which grays the color tone of the porcelain or possibly blacks it depending upon the firing conditions. Thus this is not applied at all to porcelain fired to a metal in which particular importance is attached to the aesthetic appearance. However, the modelling liquid for dental porcelain according to this invention can be well-condensed because of its viscosity being 0.1 Pa.s or less at 23° C. Moreover, it can be sintered after removal of an excessive portion with tissue papers of gauzes of the photopolymerizable or polymerizable compound having at least one ethylenically unsaturated double bond or the organic material solid or semi-solid at normal temperature. When the photopolymerizable or polymerizable compound having at least one ethylenically unsaturated double bond has a high viscosity or the photopolymerization reaction or the reaction with the organic peroxide or pyrimidinetrione and organometallic compound contained in the porcelain is very slow, the organic material solid or semi-solid at normal temperature and the photopolymerizable or polymerizable compound having at least one ethylenically unsaturated double bond are previously dissolved in an organic solvent not volatilized at room temperature but having a boiling point so high as volatilized off by heating to 100° C.–150° C. or higher. After building up and condensation, the porcelain is heated to 100° C.–150° C. or higher to remove the aforesaid organic solvent. Since the remaining organic material solid or semi-solid at normal temperature solidifies, however, it is possible to maintain the form of the porcelain as it is built up. Also, since the refractive index of the organic solvent used can be regulated in the range of 1.4 to 1.6, it is possible to make a previous estimation of the color tone of the porcelain before firing. Consequently, it is possible to obtain the porcelain fired to a metal, which assumes a color tone quite identical with that of the porcelain, as mixed with water and built up in place.

(In order to obtain dental prostheses as close to natural teeth as possible, the special effects are added to porcelains with the use of internally or externally coloring porcelain materials).

1. The modelling liquid for dental porcelain according to this invention has a refractive index of 1.4 to 1.6 at 23 C., while porcelains have a refractive index of 1.47 to 1.50. This modelling liquid undergoes no substantial change in refractive index before and after exposure to light or the reaction with the organic peroxide or pyrimidinetrione derivative and organometallic compound contained in the porcelain, i.e., before and after curing. Thus, when some are selected from a number of internally or externally coloring porcelain materials to afford the desired special effect to the porcelain, thereby expressing sophisticated color tones, even novices can make a previous estimation of the color tone of the porcelain after firing. Therefore, it is possible to prevent such failures that porcelains are cut off and re-built up as many times as is necessary due to the fact that the color tone of porcelain cannot be estimated, as is the case with mixing the porcelains with water. This makes it possible for anyone to achieve production of the special effects, which has so far been practiced by experts alone. The internally or externally coloring porcelain materials mixed with the modelling liquid according to this invention can be cured by exposure to light or reaction with the organic peroxide any pyrimidinetrione derivative and organometallic compound contained in the porcelain. This also makes it possible for anyone to build up or apply porcelains on the desired location with the desired thickness and to the desired extension. Moreover, the length of time needed for dental operation is one tenth to a few tenths of that required conventionally an the internally or externally coloring porcelain materials of the desired color tones can be selected precisely. Therefore, the special effects can be so easily imparted to porcelains that the prosthesis can be improved in the aesthetic appearance with improvements in quality an work efficiency.

2. The modelling liquid for dental porcelain according to this invention is designed to be built up by exposure to light or reaction with the organic peroxide or pyrimidinetrione and organometallic compound contained in the porcelain for its curing. Therefore, when the special effects are produced on the porcelain caused by internal or surface stains such as produced by cracking, yellowing and insufficient calcification, etc. there can be built up or coated with a fine brush. Thus it is possible for anyone to effect the required operations easily without any craftmanship. Consequently, it is possible to produce the special effects of constant quality to porcelains with internally or externally coloring porcelain materials at any desired time, since neither color mixing nor line thickening or blurring may take place, as is the case with mixing with water.

The modelling liquid according to this invention, which has a refractive index of 1.4 to 1.6 inclusive at 23° C. and a viscosity of at most 0.1 Pa.s at 23° C., may be prepared from photopolymerizable or polymerizable compounds having at least one ethylenically unsaturated double bond. Of these compounds, examples of monofunctional methacrylates and acrylates include methyl methacrylate, ethyl methacrylate, n-butyl methacrylate, iso-butyl methacrylate, t-butyl methacrylate, 2-ethylhexyl methacrylate, lauryl methacrylate, tridecyl methacrylate, stearyl methacrylate, cyclohexyl methacrylate, benzyl methacrylate, 2-hydroxyethyl methacrylate, 2-hydroxypropyl methacrylate, glycidyl methacrylate, tetrahydrofurfuryl methacrylate, allyl methacrylate, 2-ethoxyethyl methacrylate, methoxydiethylene glycol methacrylate, methoxytetraethylene glycol methacrylate, methoxypolyethylene glycol methacrylate, phenoxydiethylene glycol methacrylate, phenoxyhexaneethylene glycol methacrylate, glycerol methacrylate, tetrahydrofurfuryl methacrylate, dicyclopentenyl methacrylate, dicyclopentanyl methacrylate, iso-bornyl methacrylate, phenyl methacrylate, dipentaerythritolmonohydroxyl methacrylate, caprolactone-modified tetrahydrofurfuryl methacrylate, caprolactone-modified dipentaerythritol methacrylate, caprolactone-modified 2-hydroxyethyl methacrylate, caprolactone-modified 2-hydroxy propyl methacrylate, 2-ethoxyethyl methacrylate and lauryltridecyl methacrylate as well as their acrylates.

Examples of polyfunctional methacrylates and acrylates include ethylene glycol dimethacrylate, diethylene glycol dimethacrylate, triethylene glycol dimethacrylate, tetraethylene glycol dimethacrylate, polyethylene glycol dimethacrylate, 1,3-butylene glycol dimethacrylate, 1,6-hexanediol dimethacrylate, neopentyl glycol dimethacrylate, tripropylene glycol dimethacrylate, polypropylene glycol dimethacrylate, glycerol dimethacrylate, disphenol A dimethacrylate, bisphenol A glycidyl dimethacrylate, ethylene oxide-modified bisphenol A dimethacrylate, ethylene oxide-modified glycidyl dimethacrylate, 1,3-butanediol dimethacrylate, 1,4-butanediol dimethacrylate, 2,2-bis(methacryloxyphenyl)propane, 2,2-[4-(2-hydroxy-3-methacryloxyethoxypeny)]propane, 2,2-bis(4-methacryloxyethoxyphenyl)propane, 2,2-bis(4-methacryloxyethoxydiethoxyphenyl)propane, 2,2-bis(4-methacryloxypropoxyphenyl)propane, 7,7,9-trimethyl-4,13-dioxo-3,14-dioxo-5,12-diazahexadecane-1,6-diol dimethacrylate, neopentyl glycol hydroxypivalate ester dimethacrylate, caprolactone-modified hydroxypivalic acid neopentyl glycol ester dimethacrylate, ethylene oxide-modified bisphenol A dimethacrylate, trimethylololethane dimethacrylate, trimethylolpropane dimethacrylate, trimethylolmethane trimethacrylate, trimethylolethane trimethacrylate, trimethylolpropane trimethacrylate, pentaerythritol trimethacrylate, dipentaerythritol trimethacrylate, penaerythritol tetramethacrylate, dipentaerythritol tetramethacrylate, pentaerythritol hexamethacrylate and dipentaerythritol hexamethacrylate; compounds having the following structural formulae; and their acrylates. These compounds may be used alone or in combination of two or more, and optionally contain photopolymerization initiators, reducing agents, polymerization inhibitors, organic solvents, organic materials solid or semi-solid at normal temperature, tertiary amines, organohalogen compounds, etc.

Reaction product of 3-chloro-3-hydroxypropyl methacrylate with methylcyclohexane diisocyanate.

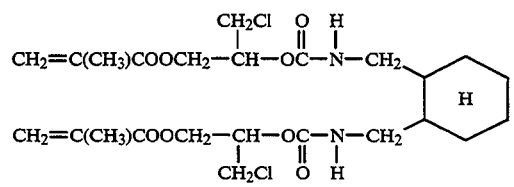

Reaction product of 2-hydroxypropyl methacrylate with trimethylhexamethylene diisocyanate.

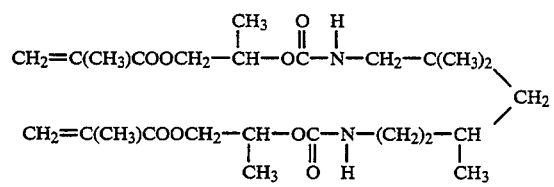

Reaction product of 2-hydroxypropyl methacrylate with methylcyclohexane diisocyanate.

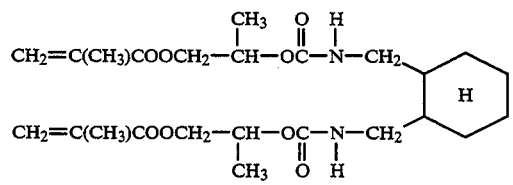

Reaction product of 2-hydroxypropyl methacrylate with methylene-bis(4-cyclohexyl isocyanate).

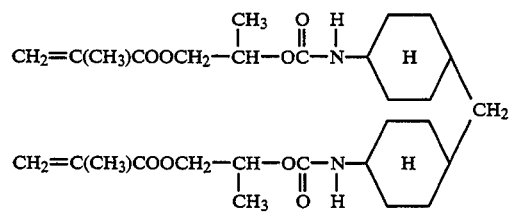

Reaction product of 2-hydroxymethyl methacrylate with trimethylhexamethylene diisocyanate.

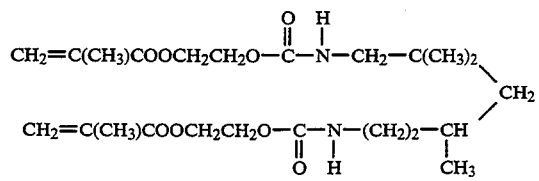

Reaction product of 2-hydroxypropyl methacrylate with isofluorodiisocyanate.

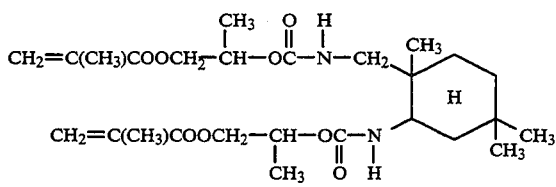

Reaction product of 3-chloro-2-hydroxypropyl methacrylate with isofluorodiisocyanate.

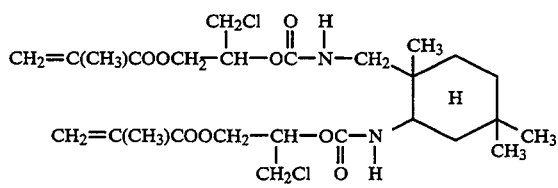

Di-(2-methacryloyoxyethyl) dihexamethylene-7-alkyl-tetracarbamate.

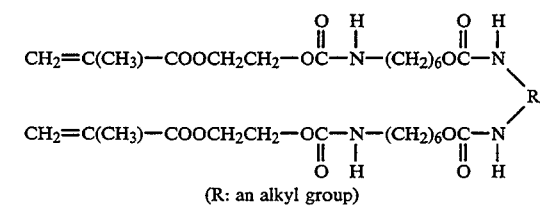

(R: an alkyl group)

Reaction product of 2-hydroxyethyl methacrylate with methylene-bis(4-cyclohexyl isocyanate).

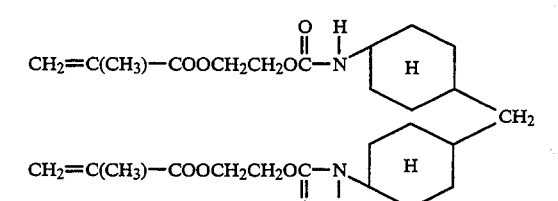

Reaction product of 3-chloro-2-hydroxypropyl methacryle with hexamethylene diisocyanate.

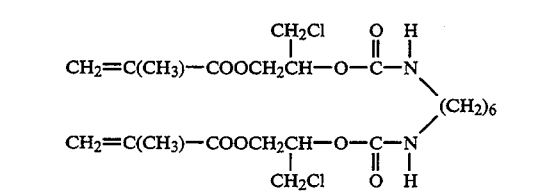

Reaction product of 2-hydroxypropyl methacrylate with hexamethylene diisocyanate.

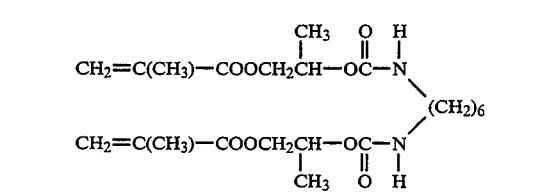

Reaction product of 2-hydroxyethyl methacrylate with hexamethylene diisocyanate.

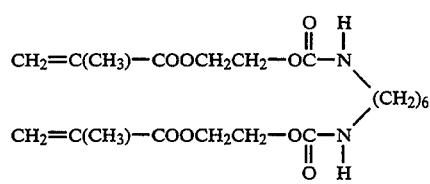

Reaction product of 2-hydroxyethyl methacrylate with isophorone diisocyanate

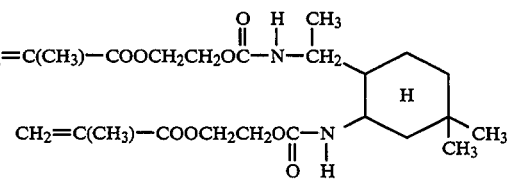

Reaction product of 2-hydroxyethyl methacrylate with methylcyclohexane diisocyanate.

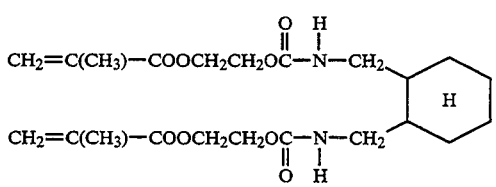

Reaction product of 2-hydroxypropyl methacrylate and glycidol dimethacrylate with isophorone diisocyanate.

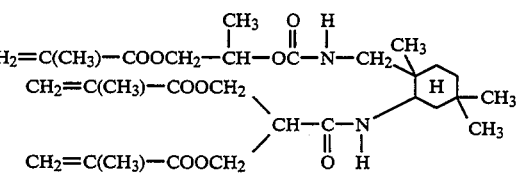

Reaction product of glycidol dimethacrylate with methylcyclohexane diisocyanate.

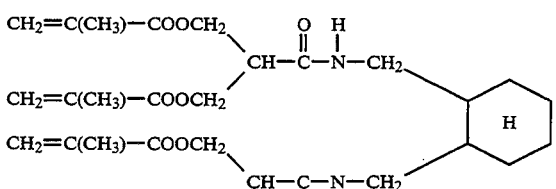

Reaction product of glycidol dimethacrylate with hexamethylene diisocyanate.

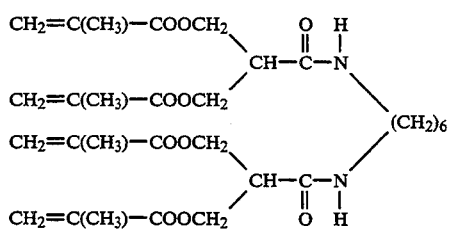

Reaction product of glycidol dimethacrylate with isophorone diisocyanate.

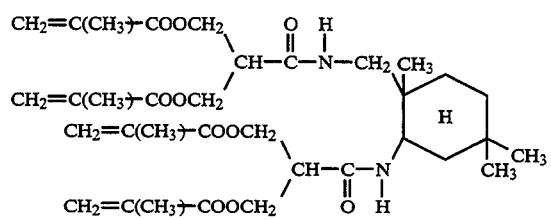

Reaction product of 2-hydroxypropyl methacrylate with methylbenzene diisocyanate.

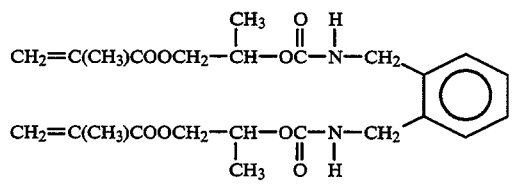

Reaction product of 3-chloro-2-hydroxypropyl methacrylate with methylbenzene diisocyanate.

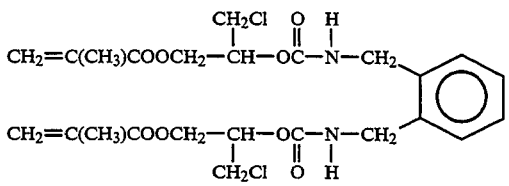

Reaction product of 2-hydroxyethyl methacrylate with methylbenzene diisocyanate.

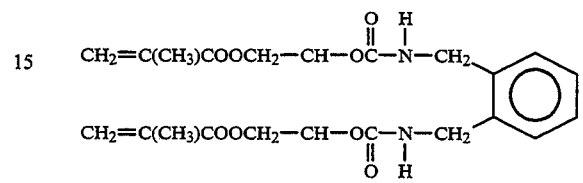

Reaction product of glycidol dimethacrylate with methylbenzene diisocyanate.

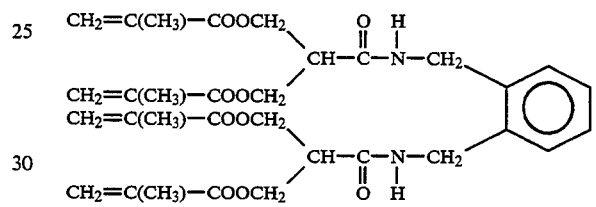

Reaction product of glycidol dimethacrylate with hexamethylane diisocyanate.

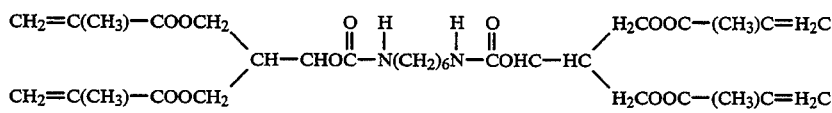

1,6-dimethacrylethyloxycarbonylaminohexylaminocarbonyloxy(3-methyl)propyloxycarbonylaminohexane

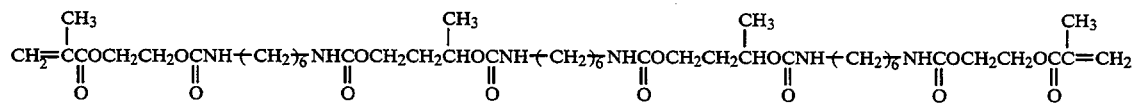

Reaction product of a hexamethylene diisocyanate addition product of a 6-hexanolide addition product of 2,2'-di(4-hydroxycyclohexyl) propane with 2-hydroxyethyl methacrylate.

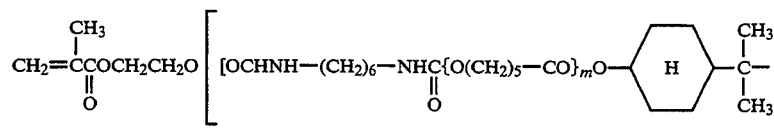

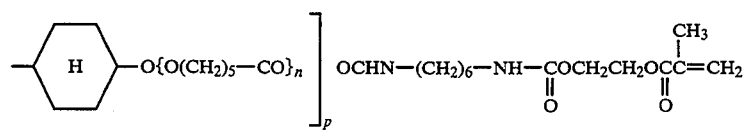

$m + n = 0\sim10$,
$m + n \approx 6$,
$p = 0\sim3$,
$p \approx 1$

The organic solvents used in this invention may advantageously be those based on hydrocarbons; halogenated hydrocarbons; alcohols; ethers/acetals; ketones; esters; polyhydric alcohols and their derivatives; and nitrogen compounds.

More illustratively, the hydrocarbon-based organic solvents may advantageously be n-pentane, n-hexane, iso-hexane, n-heptane, n-octane, iso-octane, n-decane, 2,2-dimethylbutane, petroleum ether, petroleum benzyl, ligroin, gasoline, kerosine, petroleum spirit, petroleum naphtha, 2-pentene, mixed pentenes, cyclohexane, methylcyclohexane, benzene, toluene, xylene, ethylbenzene, diethylebenzene, iso-propylbenzene, amylbenzene, diamylbenzene, triamylbenzene, tetraamylbenzene, dodecylbenzene, didodecylbenzene, amyltoluene, coal tar naphtha, solvent naphtha, p-cymene, tetralin, decalin, dipentene, turpentine oil, pinene, p-menthane, pine oil and camphor oil. Particular preference is given to n-octane, n-decane, kerosine, petroleum spirit, petroleum naphtha, ethylbenzene, diethylbenzene, iso-propylbenzene, amylbenzene, diamylbenzene, triamylbenzene tetra-amylbenzene, p-cymene, pinene and p-methane.

The halogenated hydrocarbon-based organic solvents may advantageously be methylene chloride, chloroform, carbon tetrachloride, ethylene chloride, ethylidene chloride, 1,1,1-trichloroethane, 1,1,2-trichloroethane, 1,1,1,2-tetrachloroethane, 1,1,2,2-tetrachloroethane, pentachloroethane, vinylidene chloride, 1,2-dichloroethylene, trichloroethylene, tetrachloroethylene, 1,2,3-trichloropropane, isopropyl chloride, allyl chloride, 1,2-dichloropropane, butyl chloride, amyl chloride, dichloropentane, hexyl chloride, 2-ethylhexyl chloride, ethyl bromide, ethylene bromide, tetrabromoethane, chlorobromoethane, ethylene chlorobromide, chlorobenzene, o-dichlorobenzene, 1,2,4-trichlorobenzene, bromobenzene, o-dibromobenzene, o-chlorotoluene, p-chlorotoluene, α-chloronaphthalene, chlorinated naphthalene, fluorotrichloromethane and 1,1,2-trichloro-1,2,2-trifluoroethane. Particular preference is given to 1,1,2-trichloroethane, 1,1,1,2-tetrachloroethane, 1,1,2,2-tetrachloroethane, pentachloroethane, tetrachloroethylene, 1,2,3-trichloropropane, dichloropropane, hexyl chloride, 2-ethylhexyl chloride, ethylene bromide, tetrabromoethane, chlorobromoethane, ethylene chlorobromide, chlorobenzene, o-dichlorobenzene, 1,2,4-trichlorobenzene, bromobenzene, o-dibromobenzene, o-chlorotoluene and α-chloronaphthalene.

Alcoholic organic solvents may advantageously be methanol, ethanol, n-propanol, iso-propanol, n-butanol, iso-butanol, secondary butanol, n-amyl alcohol, active amyl alcohol, iso-amyl alcohol, secondary amyl alcohol, 3-pentanol, tertiary amyl alcohol, fusel oil, n-hexanol, methylamyl alcohol, 2-ethyl butanol, n-heptanol, 2-heptanol, 3-heptanol, n-octanol, 2-octanol, 2-ethyl hexanol, 3,5,5-trimethyl hexanol, nonanol, n-decanol, undecanol, trimethylnonyl alcohol, heptadecanol, 2-methyl cyclohexanol, benzyl alcohol, glycidol, furfuryl alcohol, tetrahydrofurfuryl alcohol and abietinol, all being preferable.

The organic solvents based on ethers and acetals may advantageously be ethyl ether, dichloroethyl ether, iso-propyl ether, n-butyl ether, di-iso amyl ether, n-hexyl ether, methylphenyl ether, ethylphenyl ether, n-butylphenyl ether, amylphenyl ether, cresylmethyl ether, p-tertiary amylphenyl-n-amyl ether, ethylbenzyl ether, 1,2-propylene oxide, epichlorohydrin, diglycidyl ether, 1,4-dioxane, furan, furfural, 2-methylfuran, tetrahydrofuran, tetrahydropyran, cineole, methylal and diethyl acetal, all being preferable.

The ketone-based organic solvents may advantageously be acetone, methyl acetone, methyl ethyl ketone, methyl-n-propyl ketone, methyl-n-butyl ketone, methyl iso-butyl ketone, methyl-n-amyl ketone, methyl-n-hexyl ketone, diethyl ketone, ethyl-n-butyl ketone, di-n-propyl ketone, di-iso butyl ketone, 2,6,8-trimethyl-nonanone-4, acetone oil, acetonylacetone, diacetone alcohol, mesityl oxide, isophorone, cyclohexane, methylcyclohexane, acetophenone and dypnone, all being preferable.

The ester-based organic solvents may advantageously be methyl formate, ethyl formate, propyl formate, n-butyl formate, iso-butyl formate, amyl formate, methyl acetate, n-butyl acetate, iso-butyl acetate, secondary butyl acetate, n-amyl acetate, iso-amyl acetate, methyl iso-amyl acetate, methoxybutyl acetate, secondary hexyl acetate, 2-ethylbutyl acetate, 2-ethylhexyl acetate, cylcohexyl acetate, methylcylcohexyl acetate, benzyl acetate, methyl propionate, ethyl propionate, n-butyl propionate, isoamyl propionate, methyl butyrate, ethyl butyrate, n-butyl butyrate, isoamyl butyrate, butyl stearate, methyl acetoacetate, ethyl acetoacetate, isoamyl iso-valerate, methyl lactate, ethyl lactate, n-butyl lactate, isobutyl lactate, n-amyl lactate, isoamyl lactate, methyl benzoate, ethyl benoate, propyl benzoate, butyl benzoate, isoamyl benzoate, benzyl benzoate, ethyl cinnamate, methyl salicylate, ethyl abietate, benzyl abietate, dioctyl adipate, diethyl oxalate, dibutyl oxalate, diamyl oxalate, diethyl maloate, dibutyl tartrate, tributyl citrate, dioctyl sebacate, dimethyl phthalate, diethyl phthalate, dibutyl phthalate, di-2-ethylhexyl phthalate and dioctyl phthalate, all being preferably used.

The organic solvents based on polyhydric alcohols and their derivatives may advantageously be ethylene glycol, ethylene glycol monoethyl ether, ethylene glycol monomethyl ether acetate, ethylene glycol monoethyl ether, ethylene glycol diethyl ether, ethylene glycol monoethyl ether acetate, ethylene glycol isopropyl ether, ethylene glycol dibutyl ether, ethylene glycol monobutyl ether acetate, ethylene glycol isoamyl ether, ethylene glycol monophenyl ether, ethylene glycol monphenyl ether acetate, ethylene glycol benzyl ether, ethylene glycol monohexyl ether, methoxymethoxy ethanol, ethylene glycol monoacetate, ethylene glycol diacetate, monoester of formic acid, diester of formic acid, monoester of butyrate, diester of butyrate, diester of propionic acid, diethylene glycol, diethylene glycol monomethyl ether, diethylene glycol monoethyl ether, diethylene glycol monoethyl ether acetate, diethylene glycol monobutyl ether, diethylene glycol monobutyl ether acetate, diethylene glycol dimethyl ether, diethylene glycol methylethyl ether, diethylene glycol diethyl ether, diethylene glycol dibutyl ether, diethylene glycol acetate, triethylene glycol, triethylene glycol monomethyl ether, triethylene glycol monoethyl ether, triglycol dichloride, tetraethylene glycol, polyethylene glycol, propylene glycol, propylene glycol monomethyl ether, propylene glycol monoethyl ether, propylene glycol monobutyl ether, 1-butyoxyethoxy propanol, propylene glycol derivatives, propylene chlorohydrin, dipropylene glycol derivatives, propylene chlorohydrin, dipropylene glycol, dipropylene glycol monomethyl ether, dipropylene glycol monethyl ether, tripropylene glycol monomethyl ether, polypropylene glycol, poly(oxyethylene-oxypropylene) derivatives, trimethylene glycol, butanediol, 1,5-pentanediol, hexylene glycol, octylene glycol, glycerin, glyceryl monoacetate, glyceryl diacetate, glyceryl triacetate, glyceryl monobutyrate, glycerin ether, glycerin-α-monochlorohydrin, glycerin-α,γ -dichlorohydrin and 1,2,6-hexanetriol, all being preferably used.

The organic solvents based on nitrogen compounds may advantageously be nitromethane, nitroethane, 1-nitropropane, 2-nitropropane, nitrobenzene, 0-nitroanisole, monoethylamine, diethylamine, triethylamine, isopropylamine, di-isopropylamine, n-butylamine, n-dibutylamine, n-tributylamine, isobutylamine, di-isobutylamine, secondary butylamine, n-amylamine, diamylamine, triamylamine, secondary amylamine, secondary hexylamine, 2-ethylbutylamine, n-heptylamine, 2-ethylhexylamine, dioctylamine, ethylenediamine, propylenediamine, diethylenetriamine, tetraethylenepentamine, diethylaniline, diethylbenzylamine, monoethanolamine, diethanolamine, triethanolamine, ethyl monoethanolamine, n-butyl monoethanolamine, diethyl ethanolamine, ethyl diethanolamine, n-butyl diethanolamine, di-n-butyl ethanolamine, isopropanolamine, formamide, N,N-dimethylformamide, acetonitrile, benzonitrile, acetone cyanhydrin, pyridine, α-picoline, β-picoline, γ-picoline, 2,4-lutidine, 2,6-lutidine, quinoline, isoquinoline, morpholine and ethyl morpholine, all being preferably used. These organic solvents may be used in mixture or dissolution and alone or in combination of two or more. It is noted that this invention is not limited to the above-exemplified organic solvents. In the present invention, use may be made of any organic solvent which can easily solubilize the photopolymerizable or polymerizable compound having at least one ethylenically unsaturated double bond, takes no part in chemical reactions and vaporizes quickly at a temperature lower than the firing temperature. When the amount of porcelains to be built up is small or depends upon the incineration and firing conditions, these organic solvents may be dispensed with. Thus, the amount of the organic solvents added to 100 parts by weight of the photopolymerizable or polymerizable compound having at least one ethylenically unsaturated double bond is suitably in the range of 0 to 9900 parts by weight.

The solid or semi-solid organic materials used in this invention, for instance, may include natural waxes, petroleum waxes, coal-based synthetic waxes, polyolefinical synthetic waxes, fats and oils-based synthetic waxes and alcohol based waxes (having 13 or more carbon atoms).

Included advantageously in the natural waxes are fatty acids, fatty alcohols, hydrocarbons, triglyceride, saturated fatty acids, monoenes acids, polyenes acids, unsaturated fatty acids, hydroxy fatty acids, branched fatty acids and dibasic acids.

The petroleum waxes, for instance, may advantageously be paraffin wax, microcrystalline wax, scale wax, petrolactam wax, petroleum jelly and petroleum ceresin.

The coal-based synthetic waxes, for instance, may advantageously be montan wax, acid wax, ester wax, partially saponified ester wax and montan base type soft wax. As the polyolefinical waxes, use may advantageous be made of those based on high-, medium- and low-density polyethylene.

Included advantageously in the fats and oils-based synthetic waxes are hardened castor oil, 12-hydroxystearic acid, 12-hydroxystearic acid amide, N-(2-hydroxyethyl)-12-hydroxystearic acid amide, N,N'-ethylene-bis-12-hydroxystearic acid amide, N,N'-hexamethylene-bis-12-hydroxystearic acid amide, N,N'-xylene-bis-12-hydroxystearic acid amide, 12-hydroxystearic acid methyl, 12-hydroxystearic acid butyl, propylene glycol mono-12-hydroxystearate, glycerin monohydroxystearate, ethylene glycol mono-12-hydroxystearate, 12-hydroxystearic acid lithium, 12-hydroxystearic acid calcium, amide laurate, amide stearate, amide oleate, erucic acid amide, amide recinoleate, special fatty acid amide, N,N'-ethylene-bis-lauric acid amide, N,N'-methylene-bis-stearic acid amide, N,N'-butylene-bis-stearic acid amide, N,N'-hexamethylene-bis-stearic acid amide, N,N'-hexamethylene-bis-oleic acid amide, N,N'-xylene-bis-stearic acid amide, monomethylolamide stearate, coconut oil fatty acid monoethanaol amide, diethanolamide stearate, N-oleyl stearic acid amide, N-oleyl oleic acid amide, N-stearyl stearic acid amide, N-stearyl oleic acid amide, N-oleyl palmitic acid amide, N-stearyl erucic acid amide, N,N'-diolein adipic acid amide, N,N'-distearyl adipic acid amide, N,N'-dioleyl sebacic acid amide, N,N'-distearyl sebacic acid amide, N,N'-distearyl terephthalic acid amide, N,N'-distearyl isophthalic acid amide, diheptadecyl ketone, diundecyl ketone, dodecylamine, tetradecylamine, octadecylamine, oleylamine, dioctadecylamine, methyl laurate, methyl myristate, methyl palmitate, methyl stearate, coconut oil fatty acid methyl, isopropyl myristate, butyl stearate, octadecyl stearate, oleyl oleate, glycerin monostearate, glycerin mono-oleate, glycerin docosanoate, sorbitan monopalmitate, sorbitan monostearate, sorbitan tristearate, sorbitan mono-oleate, propylene glycol monopalmitate, propylene glycol monostearate, ethylene glycol monostearate and polyoxyethylene monostearate.

As the alcoholic waxes (having 13 carbon atoms), use may advantageously be made of, for instance, tridecyl alcohol, myristyl alcohol, pentadecyl alcohol, cetyl alcohol, heptadecyl alcohol, octadecyl alcohol, nonadecyl alcohol and aralkyl alcohol. These organic materials solid or semi-solid at normal temperature may be used in mixing or dissolving along or in combination of two or more. It is noted that this invention is not limited to the above-exemplified organic materials solid or semi-solid at normal temperature. In other words, use may be made of any organic material solid or semi-solid at normal temperature, which is even slightly soluble in the photopolymerizable or polymerizable compound having at least one ethylenically unsaturated double bond and the above-mentioned solvents, takes no part in chemical reactions at all, gives rise to no incineration residue at the firing temperature of porcelain whatsoever and has no adverse influence upon the porcelain fired to a metal after firing. Depending upon the type of the photopolymerizable or polymerizable compound having at least one ethylenically unsaturated double bond or the incineration or firing conditions, these organic materials solid or semi-solid at normal temperature may be dispensed with. Thus, the amount of the organic materials solid or semi-solid at normal temperature added to 100 parts by weight of the photopolymerizable or polymerizable compound having at least one ethylenically unsaturated double bond is suitably in the range of 0 to 900 parts by weight inclusive.

The photopolymerization initiators used in this invention may advantageously be compounds based on α-diketone, ketal, anthraquinone, thioxanthone and benzoin alkyl ether. More illustratively, d,l-camphorquinone, benzyl, diacetyl, acenaphthenequinone, 9.10-phenanthrene quinone and so on may advantageously be used as the α-diketone compounds. Particular preference, however, is given to d,l-camphorquinone and benzyl. The ketal compounds, for instance, may advantageously be benzyldimethylketal, benzyldiethylketal, benzyldipropylketal, benzyldi(β-phenylethyl)ketal, benzyldi(2-methoxyethyl)ketal, benzyl di(2-ethoxyethyl)ketal, benzyldi(2-methoxyethoxyethyl) ketal, benzyldi(2-ethoxyethoxyethyl)ketal, 4,4'-dimethylbenzyldimethylketal, 2,2'-dimethoxybenzyldiethyl ketal, 4,4'-dichlorobenzyuldiethylketal an 4,4'-dichlorobenzyldipropylketal. Particular preference, however, is given to benzyldimethylketal, benzyldiethylketal, benzyldi(2-methoxyethyl)ketal and 4,4'-dimethylbenzyldimethylketal.

The anthraquinone compounds may advantageously be anthraquinone, 1-chloroanthraquinone, 2-chloranthraquinone, 1,2-benzanthraquinone, 1-hydroxyanthraquinone, 1-methylanthraquinone, 2-ethylanthraquinone and 1-bromoanthraquinone. Particular preference, however, is given to anthraquinone, 1-chloroanthraquinone and 1,2-benzanthraquinone. Advantageously, the thioxanthone compounds may be thioxanthone, 2-chlorothioxanthone, 2-isopropylthioxanthone, 2-nitrothioxanthone, 2-methylthioxanthone, 2,4-dimethylthioxanthone, 2,4-diethylxanthone, 2,4-di-isopropylthioxanthone, 2-chloro-7-trifluoromethylthioxanthone, thioxanthone-10,10-dioxide and thioxanthone-10-oxide. Particular preference, however, is given to thioxanthone, 2-chlorothioxanthone, 2,4-dimethylxanthone, 2,4-diethylxanthone and 2,4-di-isopropylthioxanthone.

Advantageously, the benzoinalkylether compounds may be benzoinmethylether, benzoinethylether, benzoinisopropylether, benzoin-n-butylether and benzoinbutylether. Particular preference, however, is given to benzoin butylether.

The aforesaid photopolymerization initiators may be used alone or in combination of two or more.

Of these photopolymerization initiators, those based on α-diketone, anthraquinone, thioxanthone and benzoinalkylether may suitably be added in the range of 0.001 part by weight inclusive to 15 parts by weight exclusive per 100 parts by weight of the photopolymerizable compound having at least one ethylenically unsaturated double bond. At below 0.001 part by weight, any satisfactory curing properties are not obtained due to inferior photopolymerization. At 15 parts by weight or higher, the photopolymerization compound is so colored in an yellow tint inherent in the photo-polymerization initiators that when mixed with porcelain, no proper color tone is achieved.

The ketal compound may suitably be added in the range of 0.001 part by weight inclusive to 20 parts by weight exclusive per 100 parts by weight of the photopolymerizable compound having at least one ethylenically unsaturated double compound. At below 0.001 part by weight, any satisfactory curing properties are not obtained due to inferior photopolymerization. At 20 parts by weight or higher, solubility at room temperature is so substantially reached that when the temperature of the modelling liquid drops, the ketal compound precipitates off, making mixing operation difficult.

The reducing agents used in this invention serve to reduce a photosensitizer when it is excited, but is incapable of reducing it when it is not excited by active energy beams. The reducing agents may be primary, secondary or tertiary amines, as expressed by:

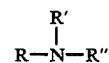

wherein two or one or none of groups R, R' and R" may be hydrogen. At least one of R, R' and R" may be an identical or different hydrocarbon group. The hydrocarbon group may then be an alkyl, cycloalkyl or hydroxyalkyl group. Preferably, R, R' and R" may be an alkyl group having 1 to 10 carbon atoms.

Suitable examples of the reducing agents, wherein at least one of units R, R' and R" is a hydrocarbon, are propylamine, n-butylamine, pentylamine, hexylamine, dimethylamine, diethylamine, dipropylamine, di-n-butylamine, dipentylamine, 2-dimethylaminoethanol, trimethylamine, triethylamine, tri-propylamine, tri-n-butylamine, tripentylamine, dimethyl-aminoethyl methacrylate, diethylaminoethyl methacrylate, triethanolamine and long-chain aliphatic amines.

Examples of the reducing agents including an aromatic group are N,N'-dimethylaniline, N,N'-dimethyl-p-toluidine, p-tolyldiethanolamine, m-tolyldiethanolamine, N-methyldiphenylamine, 2-dimethylaminobenzoic acid ethyl, 4-dimethyl-aminobenzoic acid ethyl, 4-dimethylaminobenzoic acid methyl, 4-dimethylaminobenzoic acid butyl, 4-dimethylaminobenzoic acid 2-ethylhexyl and 4-dimethylaminobenzoic acid isoamyl.

Use may also be made of a diamine having the following structural formula:

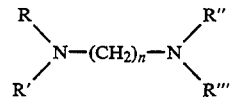

wherein n is an integer of 2 or more and groups R, R', R" and R''', which may be identical with or different from each other, each are a hydrogen atom or a hydrocarbon group, especially, an alkyl group. Examples of such reducing agents are ethylenediamine, trimethylenediamine, tetramethylenediamine, pentamethylenediamine or hexamethylenediamine or their N-hydrocarbon derivatives, especially, an N-alkyl derivative.

Examples of the reducing agents, in which the element N forms a part of the rings, are piperidine or its N-hydrocarbon derivatives. Other reducing agents, for instance, are triarylamines, allylthiourea, aromatic sulfinic acid salts and 5-alkyl or 5-allyl barbituric acid.

Of these reducing agents, preference is given to dimethylaminoethyl methacrylate, triethanolamine, 4-dimethylaminobenzoic acid methyl and 4-dimethylaminobenzoic acid ethyl. The foregoing reducing agents may be used alone or in combination of two or more.

Preferably, the amount of these reducing agents added to 100 parts by weight of the photopolymerizable compound having at least one ethylenically unsaturated double bond is in the range of 0.001 part by weight inclusive to 20 parts by weight exclusive. At below 0.001 part by weight, there is an increase in the curing time due to inferior photopolymerization. At 20 parts by weight or higher, the storage stability of the modelling liquid gets so worse that the length of time allowed for dental works under a usual indoor light is fairly reduced.

Preferably, the tertiary amines used in this invention are aromatic tertiary amines. More illustratively, N,N'-dimethyl-p-toluidine, N-dimethylaniline, N-methyl-N-β-hydroxyethylaniline, N-di(β-hydroxyethyl)-aniline and N-di(β-hydroxyethyl)-p-toluidine, although not critical, are preferred. These aromatic tertiary amines may be used in mixing or dissolving alone or in combination of two or more, and may suitably be added in the range of 0.05 parts by weight inclusive to 5 parts by weight exclusive to 100 parts by weight of the polymerizable compound having at least one ethylenically unsaturated double bond. At below 0.05 parts by weight, curing becomes so insufficient due to poor polymerization that the marginal region cannot be maintained. At 5 parts by weight or higher, on the other hand, the desired color tone of porcelain cannot be distinguished from that of the aromatic tertiary amines. Whenever using a tertiary amine-containing modelling liquid, it is essentially required that an organic peroxide be added to porcelain.

Advantageously, the organic peroxides used in this invention are benzoyl peroxide, dilauroyl peroxide, 4,4-dichlorobenzoyl peroxide, 2,4-dichlorobenzoyl peroxide and methyl ethyl ketone peroxide, although this invention is not limited to them. These organic peroxides may be used in mixing or dissolving along or in combination of two or more, and may suitably be added in the range of 0.1 part by weight inclusive to 5 parts by weight exclusive to 100 parts by weight of porcelain, if taking the reactivity of a mixture of 1.5 g of porcelain with 1 ml of the present modelling liquid. At below 0.1 part by weight, curing becomes so insufficient due to poor reactivity that the form of the marginal region cannot be maintained. At 5 parts by weight or higher, on the other hand, a room-temperature reaction proceeds so rapidly that the length of time allowed for building up is insufficient.

The organic halogen compounds used in this invention, for instance, may be dilauryl dimethylammonium chloride, lauryldimethyl-benzylammonium chloride, benzyltrimethyl-ammonium chloride, di-isobutylamine hydrochloride, tetra-n-butylammonium chloride, triethylamine hydrochloride, trimethylamine hydrochloride, dimethylamine hydrochloride, diethylamine hydrochloride, methylamine hydrochloride, ethylamine hydrochloride, isobutylamine hydrochloride, triethanolamine hydrochloride, β-phenylethylamine hydrochloride, acetylcholine chloride, 2-chlorotriethylamine, (2-chloroethyl)trimethylammonium chloride, tetradecyldimethylbenzylammonium chloride, tetraethylammonium chloride, tetramethylammonium chloride, tetrabutylammonium bromide, benzyltriethylammonium bromide, benzyltrimethyl-ammonium chloride, tetrabutylammonium fluoride and tetrabutyl-ammonium iodide, which may be used alone or in admixture. Of these organic halogen compounds, dilauryldimethylammonium chloride, lauryldimethylbenzylammonium chloride and tetra-n-butylammonium chloride are preferred, since they are soluble at normal temperature in an amount up to about 5 parts by weight in 100 parts by weight of the polymerizable compound having at least one ethylenically unsaturated double bond. Other organic halogen compounds, whose solubility is smaller at normal temperature, must be filtered for practical use. Preferably, the amount of these organic halogen compounds added to 100 parts by weight of the polymerizable compound having at least one ethylenically unsaturated double bond is in the range of 0.01 part by weight inclusive to 5 parts by weight exclusive. At below 0.01 part by weight, curing becomes so insufficient due to poor reactivity that the form of the marginal region cannot be maintained. At 5 parts by weight or higher, on the other hand, not only is th liquid colored with a color close to yellow characteristic of the organic halogen compound, but also the room temperature-reaction proceeds so rapidly that the length of working time needed for building up becomes insufficient. Whenever using an organic halogen compound-containing modelling liquid, it is essentially required that both a pyrimidinetrione derivative and an organometallic compound be added to porcelain.

The pyrimidinetrione derivatives used in this invention, for example, may include N-cyclohexyl-5-ethyl-pyrimidinetrione, N-benzyl-5-phenylpyrimidinetrione, 5-butylpyrimidinetrione, 5,5-diethylpyrimidinetrione, 1,3,5-trimethylpyrimidinetrione, 2,4,6-(1H, 3H, 5H)pyrimidinetrione and 1,3-dimethylpyrimidinetrione. Of these, the most excellent is N-cyclohexyl-5-ethyl-pyrimidinetrione. In view of the reactivity of a mixture of 1.5 g of porcelain with 1.5 ml of the present modelling liquid, the amount of these pyrimidinetrione derivatives added to 100 parts by weight of porcelain is preferably in the range of 0.1 part by weight inclusive to 10 parts by weight exclusive. At below 0.1 part by weight, curing becomes so insufficient due to poor reactivity that the form of the marginal region cannot be maintained. At 10 parts by weight or higher, on the other hand, the room-temperature reaction proceeds so rapidly that the length of time needed for building up becomes insufficient.

The organometallic compounds used in this invention may be acetylacetone copper, cupric acetate, copper oleate, acetylacetone manganese, manganese naphthenate, octylic acid manganese, acetylacetone cobalt (III), cobalt naphthenate, acetylacetone lithium, zinc naphthenate, acetylacetone nickel, nickel acetate, acetylacetone aluminium acetylacetone calcium, acetylacetone chromium (III), acetylacetone iron (III), sodium naphthenate and rare earth octoate, although this invention is not limited to them. Although used alone or in admixture, these organometallic compounds should be added to porcelain together with the pyrimidinetrione derivative. In view of the reactivity of a mixture of 1.5 g of porcelain with 1 ml of the present modelling liquid, the amount of the organometallic compound added to 100 parts by weight of porcelain is preferably in the range of 0.001 part by weight inclusive to 0.2 parts by weight exclusive. At below 0.001 part by weight, curing becomes so insufficient due to poor reactivity that the form of the marginal region cannot be maintained. At 0.2 parts by weight of higher, however, not only does the room temperature-reaction proceed so rapidly that the length of time needed for building up becomes insufficient, but the porcelain is also tinted with the color characteristic of the organometallic compound, e.g., with blue in the case of acetylacetone copper and reddish brown in the case of acetylacetone iron (III).

EXAMPLES

Modelling liquid samples according to this invention and for comparison purposes were prepared and estimated by the following experiments 1-8. It is understood that this invention is not limited to such samples. Set out in Table 1 are the results of the samples according to this invention and for comparison purposes. The experiments 1-8 were performed in the following manners.

Experiment 1—Attachability to and detachability from gypsum working model and shapeability A non shoulder metallic coping (for the maxillary central incisor tooth) was prepared on an anhydrite working model, and Unibond Margin Porcelain made by Shofu Co., Ltd. was mixed with modelling liquid samples set out in Table 1. In Examples 1-10, 14 and 15 and Comparative Examples 1-4 and 14, the samples were exposed to light from GC Light VL-1 made by GC Dental Industrial Corporation for 40 seconds. In Examples 11-25 and Comparative Examples 5-9 and 13, 30-second condensation was performed with a warm air of about 80° C. from GC Ultra Condenser UL-1 made by GC Dental Industrial Corporation and in Comparative Examples 10 and 11, condensation was carried out with the same condenser. In Comparative Example 12, 1 part by weight of Plastodent (orange) made by Degussa Company was mixed with 6 parts by weight of Unibond Margin Porcelain made by Shofu Co., Ltd., while they were melted with a gas burner. The thus formed marginal regions were attached to or detached from the anhydrite working model to make an estimation whether or not the forms of the porcelain samples were maintained. It is noted that in Examples 18-21 and Comparative Example 6 and 7 in which the present modelling liquids contained N,N'-dimethyl-p-toluidine as the tertiary amine, 0.25 parts by weight of benzoyl peroxide as the organic peroxide were previously incorporated into 100 parts by weight of Unibond Margin Porcelain made by Shofu Co., Ltd. with the use of a mortar; and in Example 22-25 and Comparative Examples 8-9 in which the present modelling liquids contained the organic halogen compound, 0.2 parts by weight of N-cyclohexyl-5-ethyl-pyrimidinetrione as the pyrimidinetrione derivative and 0.01 part by weight of acetylacetone copper as the organometallic compound were previously incorporated into 100 parts by weight of Unibond Margin Porcelain made by Shofu Co., Ltd. with the use of a mortar.

Experiment 2—Viscosity

In all the examples and comparative examples except for Comparative Example 12, viscosities were measured in a constant temperature/humidity room maintained at 23° C.± 0.5° C. and a relative humidity of 50%±5% and illuminated with red light (having an average luminous intensity of about 50 Lx) with the use of a DVL-B type Digital Viscometer made by Tokyo Keiki K.K. From a preliminary experiment, the maximum (limit) viscosity, at which porcelain could be condensed, was found to be about 0.1 Pa.s at 23° C. Thus, viscosity values lower than 0.1 Pa.s were estimated as "good" (meaning that porcelain could be condensed) and viscosity values higher than 0.1 Pa.s as "bad" (meaning that porcelain could not be condensed).

Experiment 3—Curing properties

A non shoulder metallic coping (for the maxillary central incisor tooth) was prepared, and Unibond Margin Porcelain made by Shofu K.K. was mixed with the modelling liquid samples according to this invention and for comparative purposes. After cured under the same conditions as referred to in Experiment 1, the degree of curing of the samples were estimated by letting a plastic spatula touch lightly them.

Experiment 4—State after incineration and firing

Test disc pieces, each of 15 mm in diameter and 2 mm in thickness, were previously prepared with GC Ceramibond E58 made by GC Toshi Kogyo Corporation. In all examples and comparative examples except for Comparative Example 12, the test discs were coated on their one side with single layers of the modelling liquid samples by means of a brush. Subsequently, a mixture of 0.15 g of GC Ceramibond E58 with 0.1 ml of each modelling liquid sample was built up over each test disc to a thickness of about 1 mm by means of an exclusive brush. In Comparative Example 12, 6 parts by weight of GC Ceramibond E58 was mixed with 1 part by weight of Plastodent (orange) made by Degussa K.K., while they were melted with a gas burner and the mixture was built up in the same manner as described above. For incineration and firing, each of the thus obtained samples was preliminary dried at 150° C. for 5 minutes, then heated at 600° C. for 1 minute and heated under a reduced pressure of 730 mmHg from 600° C. to 830° C. at a heating rate of 60° C. per minute, and finally retained at 830° C. for 1 minute with the use of Porcelain Furnace KDF Master Spirit 120 made by Denken K.K. For estimation, the samples were visually observed in terms of blackening due to carbon residues, cracking, change in color tone, etc. It is understood that in Examples 18-21 and Comparative Example 6 and 7 in which the present modelling liquids contained N,N'-dimethyl-p-toluidine as the tertiary amine, 0.25 parts by weight of benzoyl peroxide as the organic peroxide were previously incorporated into 100 parts by weight of GC Ceramibond E58 with the use of a mortar; and in Example 22-25 and Comparative Examples 8-9 in which the present modelling liquids contained the organic halogen compound, 0.2 parts by weight of N-cyclohexyl-5-ethyl-pyrimidinetrione as the pyrimidinetrione derivative and 0.01 part by weight of acetylacetone copper as the organometallic compound were previously incorporated into 100 parts by weight of GC Ceramibond E58 with the use of a mortar.

Experiment 5—Color tones of the modelling liquid before mixing with porcelains

In order to make for comparison a visual estimation of the color tones of the modelling liquid samples according to this invention, the color tone thereof before mixing with porcelains, was visually estimated, about 1 ml of each sample was added dropwise into a dent in G-CERA Pallet O (dry) made by GC Toshi Kogyo Corporation, which looked white under a standard light source C. Colorless and transparent tones were estimated and termed as "good".

Experiment 6—Refractive index in all examples and comparative examples except for Comparative Example 12, the refractive indices were measured in a constant temperature/humidity chamber maintained at 23° C.±0.5° C. and a relative humidity of 50%±5% with a precise Abbe Refractometer type 3 made by Atago K.K. It was found from preliminary experiments that because the refractive index of porcelains lies at 1.47–1.50, the modelling liquids are visually in coincidence with porcelains, when they have a refractive index of 1.4–1.6.

Experiment 7—Color tone reproducibility when mixed with GC Ceramibond M67 made by GC Toshi Corporation GC Ceramibond M67 was mixed for comparison with the modelling liquid samples according to this invention. Then, the color tones of the mixtures before cured by exposure to light, drying and heating were compared under a standard light source C with that of a the firing porcelain of GC Ceramibond M67 with pure water. It was estimated as "good" when the color tones of the mixtures under test were visually in coincidence with the firing porcelain of GC Ceramibond M67 with pure water.

Experiment 8—Time allowed for dental operations

About 1 ml of each of the modelling liquid samples according to this invention was added dropwise for comparison into a dent in G-CERA Pallet O (dry) made by GC Toshi Kogyo Corporation, and was then allowed to stand in a constant temperature/humidity chamber maintained at 23° C.±0.5° C. and a relative humidity of 50%±5% under usual indoor illumination (about 300 Lx) for 5 hours or more. Observation was made whether or not the samples were too hardened for use.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| A photopolymerizable or polymerizable compound having at least one ethylenically unsaturated double bond | Monofunctional | 2-hydroxyethyl methacrylate | 80 | 50 | 20 | 20 | 50 | 60 | 60 | 60 | 50 |
| | | Phenoxyethylacrylate | 20 | 50 | | 20 | | | | | 50 |
| | Polyfunctional | Ethylene glycol dimethacrylate | | | 80 | 60 | 50 | 40 | 40 | 40 | |
| | | Trimethylolpropan triacrylate | | | | | | | | | |
| Organic solvent | Based on hydrocarbon | Iso-propylbenzene | | | | | 100 | | | | |
| | Based on halogenated hydrocarbon | Tetrachloroethylene | | | | | | | | | |
| | | 1,2,3-trichloropropane | | | | | | | | | |
| | Based on alcohol | 2-methyl cyclohexanol | | | | | | | | | 20 |
| | Based on ethers acetals | Methylphenyl ether | | | | | | | 120 | 100 | |
| | | o-cresylmethyl ether | | | | | | | | | |
| | Based on ketone | Isophorone | | | | | | | | | |
| | Based on esters | Methyl benzoate | | | | | | | | | |
| | Based on polyhydric alcohol | Propylene glycol monoethyl ether | | | | | | | | | 80 |
| | Based on nitrogen compounds | Monoethanolamine | | | | | | 100 | | | |
| Organic materials solid or semi-solid at normal temperature | Natural wax | Cera alba | | | | | | | | | |
| | Petroleum wax | Microcrystalline wax | | | | | | | | 0.5 | 1 |
| | Coal-based synthetic wax | Fisher-Tropsch wax | | | | | | | | | |
| | Polyolefinical synthetic was | High-density polyethylene wax | | | | | | | | | |
| | Fats and oils-based synthetic wax | Hardened castor oil | | | | | | | | | |
| | Alcoholic waxes having 13 or more carbon atoms | Myristyl alcohol | | | | | | | | | |
| Photopolymerization initiator | Based on α-diketone | Camphor quinone | 0.01 | 0.01 | 0.005 | 0.005 | 0.01 | 0.02 | | | |
| | Based on ketal | Benzyl dimethyl ketal | | | | | | | | | |
| | Based on anthraquinone | 1,2-benzanthraquinone | | | | | | | 0.02 | | |
| | Based on thioxanthone | Thioxanthone | | | | | | | | 0.02 | |
| | Based on benzoin alkyl ether | Bezoin isopropyl ether | | | | | | | | | 0.02 |
| Reducing agent | | Dimethylaminoethyl methacrylate | 0.01 | 0.01 | 0.01 | 0.01 | 0.01 | 0.01 | 0.01 | 0.01 | 0.01 |
| | | 4-dimethylaminobenzoate methyl | | | | | | | | | |
| Tertiary amine | | N,N'-dimethyl-p-toluidine (NB 1) | | | | | | | | | |
| Organic halogen compound | | Dilauryldimethylammonium chloride (NB 2) | | | | | | | | | |
| Polymerization inhibitor | | Butylhydroxytoluene | 0.03 | 0.03 | 0.03 | 0.03 | 0.03 | 0.03 | 0.03 | 0.03 | 0.03 |
| Evaluation items | Attachability and shapeability of porcelain from gypsum models | | Good | Good | Good | Good | Good | Good | Good | Good | Good |
| | Viscosity (23° C., DVL-B type Digital Viscometer made by Tokyo Keiki K. K.) Pa · s | | 0.00672 | 0.00499 | 0.00269 | 0.00528 | 0.00287 | 0.01400 | 0.02531 | 0.01404 | 0.04000 |
| | Curing properties (Sense of touch by spatula) | | Good | Good | Good | Good | Good | Good | Good | Good | Good |
| | State of porcelain after incineration and firing (150° C., 5 minutes-600° C., 1 minute-830° C., 1 minute 730 mmHg) | | Good | Good | Good | Good | Good | Good | Good | Good | Good |
| | Colortones of modelling liquid before mixing with porcelain | | Colorless/ transparent | Colorless/ transparent | Colorless/ transparent | Colorless/ transparent | Colorless/ transparent | Colorless/ transparent | Colorless transparent | Colorless/ transparent | Colorless/ transparent |
| | Refractive index (23° C., precise Abbe refractometer type three made by Atago K. K.) | | 1.4525 | 1.4545 | 1.4545 | 1.4640 | 1.4695 | 1.4530 | 1.4796 | 1.4872 | 1.4951 |
| | Color rendition when mixed with GC Ceramibond M67 | | Good | Good | Good | Good | Good | Good | Good | Good | Good |
| | Length of time needed for technical operation (under ordinary room lighting: Approx 300LX) | | Over 5 hours | Over 5 hours | Over 5 hours | Over 5 hours | Over 5 hours | Over 5 hours | Over 5 hours | Over 5 hours | Over 5 hours |

TABLE 1-continued

| | | | Example 10 | Example 11 | Example 12 | Example 13 | Example 14 | Example 15 | Example 16 | Example 17 | Example 18 |
|---|---|---|---|---|---|---|---|---|---|---|---|
| A photopolymerizable or polymerizable compound having at least one ethylenically unsaturated double bond | Monofunctional | 2-hydroxyethyl methacrylate | 20 | 90 | 50 | 60 | 90 | 50 | 50 | | 60 |
| | | Phenoxyethylacrylate | | | | | | | | | |
| | Polyfunctional | Ethylene glycol dimethacrylate | 80 | 10 | 50 | 40 | 10 | 50 | 50 | | 40 |
| | | Trimethylolpropan triacrylate | | | | | | | | | |
| Organic solvent | Based on hydrocarbon | Iso-propylbenzene | | 150 | | | | | | | |
| | Based on halogenated hydrocarbon | Tetrachloroethylene | | | 100 | | | | | | |
| | | 1,2,3-trichloropropane | | | 50 | | | | | | |
| | Based on alcohol | 2-methyl cyclohexanol | | | | | | | | | |
| | Based on ethers acetals | Methylphenyl ether | | | | | | | | 100 | |
| | | o-cresylmethyl ether | | | | | | | | | |
| | Based on ketone | Isophorone | 50 | | | | | | | | |
| | Based on esters | Methyl benzoate | | | 50 | | | | | | |
| | Based on polyhydric alcohol | Propylene glycol monoethyl ether | 50 | | | | | | | | |
| | Based on nitrogen compounds | Monoethanolamine | | | | | | | | | |
| Organic materials solid or semi-solid at normal temperature | Natural wax | Cera alba | | | | | | | | | |
| | Petroleum wax | Microcrystalline wax | | | | | | | | | |
| | Coal-based synthetic wax | Fisher-Tropsch wax | 2 | | | | | | | | |
| | Polyolefinical synthetic was | High-density polyethylene wax | | 0.5 | | | 0.5 | | | | |
| | Fats and oils-based synthetic wax | Hardened castor oil | | 3.5 | | | 3.5 | | | | |
| | Alcoholic waxes having 13 or more carbon atoms | Myristyl alcohol | 0.01 | | 150 | 100 | | | | | |
| Photopolymerization initiator | Based on α-diketone | Camphor quinone | | | 150 | 4.5 | | | | | |
| | Based on ketal | Benzyl dimethyl ketal | | | | | | | | | |
| | Based on anthraquinone | 1,2-benzanthraquinone | | | | | | 0.01 | | | |
| | Based on thioxanthone | Thioxanthone | | | | | | | | | |
| | Based on benzoin alkyl ether | Bezoin isopropyl ether | 0.005 | | | | | | | | |
| Reducing agent | | Dimethylaminoethyl methacrylate | | | | | | | | | |
| | | 4-dimethylaminobenzoate methyl | | | | | | 5.0 | | | |
| Tertiary amine | | N,N'-dimethyl-p-toluidine (NB 1) | | | | | 0.01 | | | | |
| Organic halogen compound | | Dilauryldimethylammonium chloride (NB 2) | | | | | | | | 0.1 | |
| Polymerization inhibitor | | Butylhydroxytoluene | 0.03 | 0.03 | 0.03 | 0.03 | 0.03 | 0.03 | 0.03 | 0.03 | 0.03 |
| Evaluation items | Attachability and shapeability of porcelain from gypsum models | | Good | Good | Good | Good | Good | Good | Good | Good | Good |
| | Viscosity (23° C., DVL-B type Digital Viscometer made by Tokyo Keiki K. K.) Pa·s | | 0.00308 | 0.00310 | 0.00255 | 0.01150 | 0.00643 | 0.00499 | 0.00877 | 0.02235 | 0.00520 |
| | Curing properties (Sense of touch by spatula) | | Good | Good | Good | Good | Good | Good | Good | Good | Good |
| | State of porcelain after incineration and firing (150° C., 5 minutes-600° C., 1 minute-830° C., 1 minute 730 mmHg) | | Good | Good | Good | Good | Good | Good | Good | Good | Good |
| | Colortones of modelling liquid before mixing with porcelain | | Colorless/ transparent | Colorless/ transparent | Colorless/ transparent | Colorless/ transparent | Colorless/ transparent | Colorless/ transparent | Colorless/ transparent | Colorless/ transparent | Colorless/ transparent |
| | Refractive index (23° C., precise Abbe refractometer type three made by Atago K. K.) | | 1.4458 | 1.4831 | 1.4792 | 1.4685 | 1.4383 | 1.4551 | 1.4295 | 1.4612 | 1.4533 |
| | Color rendition when mixed with GC Ceramibond M67 | | Good | Good | Good | Good | Good | Good | Good | Good | Good |
| | Length of time needed for technical operation (under ordinary room lighting: Approx 300LX) | | Over 5 hours | Over 5 hours | Over 5 hours | Over 5 hours | Over 5 hours | Over 5 hours | Over 5 hours | Over 5 hours | Over 5 hours |

TABLE 1-continued

| | | | Example 19 | Example 20 | Example 21 | Example 22 | Example 23 | Example 24 | Example 25 | Comparative Example 1 |
|---|---|---|---|---|---|---|---|---|---|---|
| A photopolymerizable or polymerizable compound having at least one ethylenically unsaturated double bond | Monofunctional | 2-hydroxyethyl methacrylate | 60 | 50 | 50 | 60 | 60 | 50 | 50 | 30 |
| | | Phenoxyethylacrylate | | | | | | | | |
| | Polyfunctional | Ethylene glycol dimethacrylate | 40 | 50 | 50 | 40 | 40 | 50 | 50 | 20 |
| | | Trimethylolpropan triacrylate | | | | | | | | |
| Organic solvent | Based on hydrocarbon | Iso-propylbenzene | | | | | | | | |
| | Based on halogenated hydrocarbon | Tetrachloroethylene | | | 100 | | | | 100 | |
| | | 1,2,3-trichloropropane | | | 50 | | | | 50 | |
| | Based on alcohol | 2-methyl cyclohexanol | | | | | | | | |
| | Based on ethers acetals | Methylphenyl ether | | | | | | | | |
| | | o-cresylmethyl ether | | | | | | | | |
| | Based on ketone | Isophorone | | | | | | | | |
| | Based on esters | Methyl benzoate | | | | | | | | |
| | Based on polyhydric alcohol | Propylene glycol monoethyl ether | | | | | | | | |
| | Based on nitrogen compounds | Monoethanolamine | 100 | | | 100 | | | | |
| Organic materials solid or semi-solid at normal temperature | Natural wax | Cera alba | | | | | | | | |
| | Petroleum wax | Microcrystalline wax | | | | | | | | |
| | Coal-based synthetic wax | Fisher-Tropsch wax | | | | | | | | |
| | Polyolefinical synthetic was | High-density polyethylene wax | | 0.5 | | | | 0.5 | | |
| | Fats and oils-based synthetic wax | Hardened castor oil | | 3.5 | | | | 3.5 | | |
| | Alcoholic waxes having 13 or more carbon atoms | Myristyl alcohol | | | 150 | | | | 150 | |
| Photopolymerization initiator | Based on α-diketone | Camphor quinone | | | | | | | | 0.0005 |
| | Based on ketal | Benzyl dimethyl ketal | | | | | | | | |
| | Based on anthraquinone | 1,2-benzanthraquinone | | | | | | | | |
| | Based on thioxanthone | Thioxanthone | | | | | | | | |
| | Based on benzoin alkyl ether | Bezoin isopropyl ether | | | | | | | | |
| Reducing agent | | Dimethylaminoethyl methacrylate | 3.5 | 0.05 | 0.05 | 0.1 | 4.0 | 0.01 | 0.01 | 0.01 |
| | | 4-dimethylaminobenzoate methyl | | | | | | | | |
| Tertiary amine | | N,N'-dimethyl-p-toluidine (NB 1) | | | | | | | | |
| Organic halogen compound | | Dilauryldimethylammonium chloride (NB 2) | | | | | | | | |
| Polymerization inhibitor | | Butylhydroxytoluene | 0.03 | 0.03 | 0.03 | 0.03 | 0.03 | 0.03 | 0.03 | 0.03 |
| Evaluation items | Attachability and shapeability of porcelain from gypsum models | | Good | Good | Good | Good | Good | Good | Good | Bad |
| | Viscosity (23° C., DVL-B type Digital Viscometer made by Tokyo Keiki K. K.) Pa · s | | 0.01398 | 0.00880 | 0.00255 | 0.00520 | 0.01400 | 0.00885 | 0.00261 | 0.00672 |
| | Curing properties (Sense of touch by spatula) | | Good | Good | Good | Good | Good | Good | Good | Bad |
| | State of porcelain after incineration and firing (150° C., 5 minutes-600° C., 1 minute-830° C., 1 minute 730 mmHg) | | Good | Good | Good | Good | Good | Good | Good | Good |
| | Colortones of modelling liquid before mixing with porcelain | | Colorless/ transparent | Colorless/ transparent | Colorless/ transparent | Colorless/ transparent | Colorless/ transparent | Colorless/ transparent | Colorless/ transparent | Colorless/ transparent |
| | Refractive index (23° C., precise Abbe refractometer type three made by Atago K. K.) | | 1.4530 | 1.4551 | 1.4792 | 1.4533 | 1.4530 | 1.4551 | 1.4792 | 1.4525 |
| | Color rendition when mixed with GC Ceramibond M67 | | Good | Good | Good | Good | Good | Good | Good | Good |
| | Length of time needed for technical operation (under | | Over | Over | Over | Over | Over | Over | Over | Over |

TABLE 1-continued ordinary room lighting: Approx 300LX

| | | | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| | | | 5 hours | 5 hours | 5 hours | 5 hours | 5 hours | 5 hours | 5 hours |
| A photopolymerizable or polymerizable compound having at least one ethylenically unsaturated double bond | Monofunctional | 2-hydroxyethyl methacrylate | 50 | 20 | 20 | 50 | 60 | 60 | 50 |
| | | Phenoxyethylacrylate | | | 20 | | | | |
| | Polyfunctional | Ethylene glycol dimethacrylate | 50 | 80 | 60 | 50 | 40 | 40 | 50 |
| | | Trimethylolpropan triacrylate | | | | | | | |
| Organic solvent | Based on hydrocarbon | Iso-propylbenzene | | | | | | | |
| | Based on halogenated hydrocarbon | Tetrachloroethylene | | | | | | | |
| | | 1,2,3-trichloropropane | | | | | | | |
| | Based on alcohol | 2-methyl cyclohexanol | | | | 100 | | | |
| | Based on ethers acetals | Methylphenyl ether | | | | | | | |
| | | o-cresylmethyl ether | | | | | | | |
| | Based on ketone | Isophorone | | | | | | | |
| | Based on esters | Methyl benzoate | | | | | | | |
| | Based on polyhydric alcohol | Propylene glycol monoethyl ether | | | | | | | |
| | Based on nitrogen compounds | Monoethanolamine | | | | | | 100 | |
| Organic materials solid or semi-solid at normal temperature | Natural wax | Cera alba | | | | | | | |
| | Petroleum wax | Microcrystalline wax | | | | | | | |
| | Coal-based synthetic wax | Fisher-Tropsch wax | | | | | | | 0.5 |
| | Polyolefinical synthetic was | High-density polyethylene wax | | | | | | | |
| | Fats and oils-based synthetic wax | Hardened castor oil | | | | | | | 3.5 |
| | Alcoholic waxes having 13 or more carbon atoms | Myristyl alcohol | | | | | | | |
| Photopolymerization initiator | Based on α-diketone | Camphor quinone | 6 | 0.01 | 0.01 | | | | |
| | Based on ketal | Benzyl dimethyl ketal | | | | | | | |
| | Based on anthraquinone | 1,2-benzanthraquinone | | | | | | 6 | |
| | Based on thioxanthone | Thioxanthone | | | | | | | |
| | Based on benzoin alkyl ether | Bezoin isopropyl ether | | | | | | | |
| Reducing agent | | Dimethylaminoethyl methacrylate | | | | | | | |
| | | 4-dimethylaminobenzoate methyl | 0.01 | 0.0005 | 12 | 0.03 | 0.01 | | 0.005 |
| Tertiary amine | | N,N'-dimethyl-p-toluidine (NB 1) | | | | | | | |
| Organic halogen compound | | Dilauryldimethylammonium chloride (NB 2) | | | | | | | |
| Polymerization inhibitor | | Butylhydroxytoluene | 0.03 | 0.03 | 0.03 | 0.03 | 0.03 | 0.03 | 0.03 |
| Evaluation items | Attachability and shapeability of porcelain from gypsum models | | Good | Bad | Good | Bad | Bad | Good | Bad |
| | Viscosity (23° C., DVL-B type Digital Viscometer made by Tokyo Keiki K. K.) Pa · s | | 0.00499 | 0.00269 | 0.00528 | 0.01370 | 0.00515 | 0.01399 | 0.00878 |
| | Curing properties (Sense of touch by spatula) | | Good | Bad | Good | Not cured | Bad | Good | Bad |
| | State of porcelain after incineration and firing (150° C., 5 minutes-600° C., 1 minute-830° C., 1 minute 730 mmHg) | | Good | Good | Good | Good | Good | Good | Good |
| | Colortones of modelling liquid before mixing with porcelain | | Yellow/ transparent | Colorless/ transparent | Yellow/ transparent | Colorless/ transparent | Colorless/ transparent | Yellow/ transparent | Colorless/ transparent |
| | Refractive index (23° C., precise Abbe refractometer type three made by Atago K. K.) | | 1.4545 | 1.4545 | 1.4640 | 1.4555 | 1.4533 | 1.4530 | 1.4550 |
| | Color rendition when mixed with GC Ceramibond M67 | | Bad | Good | Bad | Good | Good | Bad | Good |

TABLE 1-continued

| | | | Comparative Example 9 | Comparative Example 10 | Comparative Example 11 | Comparative Example 12 | Comparative Example 13 | Comparative Example 14 |
|---|---|---|---|---|---|---|---|---|
| Length of time needed for technical operation (under ordinary room lighting: Approx 300LX) | | | About 10 minutes | Over 5 hours | About 10 minutes | Over 5 hours | About 3 minutes | Over 5 hours |
| A photopolymerizable or polymerizable compound having at least one ethylenically unsaturated double bond | Monofunctional | 2-hydroxyethyl methacrylate Phenoxyethylacrylate | 50 | | | | | Spectrum Shoulder Porcelain VLC Medium made by Dentsply Co., Ltd. (Liquid curable be emission of light) |
| | Polyfunctional | Ethylene glycol dimethacrylate Trimethylolpropan triacrylate | 50 | | | | | |
| Organic solvent | Based on hydrocarbon | Iso-propylbenzene | | | | Case where 1 part of weight of Plastodent (orange wax) made by Degussa K.K. is melted for blending | SM Liquid made by Ducera Co., Ltd. (a liquid curable by heating) | |
| | Based on halogenated hydrocarbon | Tetrachloroethylene 1,2,3-trichloropropane | 100 | | Pure water Case where use was made of Margin Separator made by Ishifuku Kinzoku K.K. for the gypsum working model | | | |
| | Based on alcohol | 2-methyl cyclohexanol | 50 | | | | | |
| | Based on ethers acetals | Methylphenyl ether o-cresylmethyl ether | | | | | | |
| | Based on ketone | Isophorone | | | | | | |
| | Based on esters | Methyl benzoate | | | | | | |
| | Based on polyhydric alcohol | Propylene glycol monoethyl ether | | | | | | |
| | Based on nitrogen compounds | Monoethanolamine | | Pure water Case where no separating material is used for the gypsum working model | | | | |
| Organic materials solid or semi-solid at normal temperature | Natural wax | Cera alba | | | | | | |
| | Petroleum wax | Microcrystalline wax | | | | | | |
| | Coal-based synthetic wax | Fisher-Tropsch wax | | | | | | |
| | Polyolefinical synthetic wax | High-density polyethylene wax | | | | | | |
| | Fats and oils-based synthetic wax | Hardened castor oil | | | | | | |
| | Alcoholic waxes having 13 or more carbon atoms | Myristyl alcohol | 150 | | | | | |
| Photopolymerization initiator | Based on α-diketone | Camphor quinone | | | | | | |
| | Based on ketal | Benzyl dimethyl ketal | | | | | | |
| | Based on anthraquinone | 1,2-benzanthraquinone | | | | | | |
| | Based on thioxanthone | Thioxanthone | | | | | | |
| | Based on benzoin alkyl ether | Bezoin isopropyl ether | | | | | | |
| Reducing agent | | Dimethylaminoethyl methacrylate | 6 | | | | | |
| Tertiary amine | | N,N-dimethyl-p-toluidine (NB 1) 4-dimethylaminobenzoate methyl | | | | | | |
| Organic halogen compound | | Dilauryldimethylammonium chloride (NB 2) | | | | | | |
| Polymerization inhibitor | | Butylhydroxytoluene | 0.03 | | | | | |
| Evaluation items | Attachability and shapeability of porcelain from gypsum models | | Good | Good | Bad | Good | Bad | Good |
| | Viscosity (23° C., DVL-B type Digital Viscometer made by Tokyo Keiki K. K.) Pa · s | | 0.00250 | 0.00936 | 0.00936 | — | 0.00922 | 0.97997 |
| | Curing properties (Sense of touch by spatula) | | Good | Not cured Good | Not cured Good | Good Bad | Good Good | Good Bad |
| | State of porcelain after incineration and firing (150° C., 5 minutes-600° C., 1 minute-830° C., 1 minute 730 mmHg) | | Good | | | | | |
| | Colortones of modelling liquid before mixing with porcelain three made by Atago K. K.) | | Yellow/ transparent | Colorless/ transparent | Colorless/ transparent | Orange | Colorless/ transparent | Yellow/ transparent |
| | Refractive index (23° C., precise Abbe refractometer type | | 1.4791 | 1.3327 | 1.3327 | — | 1.3381 | 1.4800 |

TABLE 1-continued

| | | | | | |
|---|---|---|---|---|---|
| Color rendition when mixed with GC Ceramibond M67 | Bad | Bad | Bad | Bad | Bad |
| Length of time needed for technical operation (under ordinary room lighting: Approx 300LX) | About 5 minutes | Over 5 hours | Over 5 hours | 1-2 minutes | About 2 hours |
| | | | | over 5 hours | |

(NB 1) In the case where modelling liquids in which N,N'-dimethyl-p-toluidine was used, use was made of 0.25 parts by weight of benzoyl peroxide as an organic peroxide previously incorporated with a use of a mortar into 100 parts by weight of a porcelain material of the evaluation items.
(NB 2) In the case where modelling liquids in which dilaurylmethylammonium chloride was used, use was made of 0.2 parts by weight of N-cyclohexyl-5-ethylpyrimidine-trione as a pyrimidinetrione derivative and 0.01 parts by weight of acetylacetone copper as an organometallic compound previously incorporated with a use of a mortar into 100 parts by weight of a porcelain materil of the evaluation items.

The modelling liquid samples of Examples 1–4 each comprise the photopolymerizable compound having at least one ethylenically unsaturated double bond, photopolymerization initiator, reducing agent and polymerization inhibitor; Examples 5–7 each comprise the photopolymerizable compound having at least one ethylenically unsaturated double bond, organic solvent, photopolymerization initiator, reducing agent and polymerization inhibitor; Examples 8–10 each comprise the photopolymerizable compound having at least one ethylenically unsaturated double bond, organic solvent, organic material solid or semi-solid at normal temperature, photopoly-merization initiator, reducing agent and polymerization inhibitor; Examples 11–13 each comprise the photopoly-merizable or polymerizable compound having at least one ethylenically unsaturated double bond, organic solvent, organic material solid or semi-solid at normal temperature and polymerization inhibitor; Examples 14–15 each comprises the photopoly-merizable compound having at least one ethylenically unsaturated double bond, organic material solid or semi-solid at normal temperature, photopolymerization initiator, reducing agent and polymerization inhibitor, Example 16 comprises the photopolymerizable or polymerizable compound having at least one ethylenically unsaturated double bond, organic material solid or semi-solid at normal temperature and polymerization inhibitor; Example 17 comprises the organic solvent and organic material solid or semi-solid at normal temperature; Examples 18–21 each comprise the polymerizable compound having at least one ethylenically unsaturated double bond and N,N'-dimethyl-p-toluidine as the tertiary amine which allowed it to react with the organic peroxide added to porcelains to for curing; and Examples 22–25 each comprise the polymerizable compound having at least one ethylenically unsaturated double bond and dilauryldimethylammonium chloride as the organic halogen compound which allowed it to react with the pyrimidinetrione derivative and organometallic compound added to porcelains for curing. The modelling liquids according to Example Nos. 1–10 and 14–15 are cured when exposed to light, while those according to Example Nos. 11–13 and 16–17 are cured by allowing the organic material solid or semi-solid at normal temperature to be precipitated off by the volatilization of the organic solvent or the photopolymerizable or polymerizable compound having at least one ethylenically unsaturated double bond. The modelling liquids according to Example Nos. 18–25 are cured by the reaction of the polymerization promoter contained therein with the polymerization initiator contained in porcelain being not exposed to light. In Examples 3–4 the amount of the photopolymerization initiator incorporated is smaller, while in Example 14 the amount of the photopolymerization initiator incorporated is larger. In Example 10 the amount of the reducing agent contained is smaller, while in Example 15 the amount of the reducing agent contained is larger. In Example 19 the amount of the tertiary amine incorporated is smaller, while in Example 20 the amount of the tertiary amine incorporated is larger. In Example 23 the amount of the organic halogen compound added is smaller, while in Example 22 the amount of the organic halogen compound added is larger. However, since these examples are all within the ranges defined in the appended claims, the amounts being smaller or larger than the central value of the range, no problem arise in connection with the properties estimated. In Example 17, no polymerization inhibitor is added due to the absence of the photopolymerizable or polymerizable compound having at least one ethylenically unsaturated double bond. All the modelling liquids according to the examples are satisfactory in terms of the properties estimated.

Comparative Examples 1–4 were carried out so as to define the amounts of the photopolymerization initiator and reducing agent, while Comparative Examples 6–9 were performed so as to define the amounts of the tertiary amine and organic halogen compound. In Comparative Example 1 the amount of the photopolymerization initiator is smaller than the lower limit defined in the claim, while in Comparative Example 2 the amount of the photopolymerization initiator is larger than the upper limit defined in the claims. In Comparative Example 3 the amount of the reducing agent is smaller than the lower limit defined in the claim, while in Comparative Example 4 the amount of the reducing agent is larger than the upper limit defined in the claim. When the amounts of the initiator and reducing agent are smaller than the lower limits, curing by exposure to light gets so worse that the attachability or detachability of the porcelain to or from the gypsum working model is inferior with a decrease in its shapeability. When they are larger than the upper limits, on the other hand, the modelling liquids assume a yellow tone before mixing with porcelains. Further, under an ordinary indoor light, the reactivity of the modelling liquids with light is so high that when mixed with porcelains, they start to cure immediately and so cannot be used. In Comparative Example 6 the amount of the tertiary amine is smaller than the lower limit defined in the claim, while in Comparative Example 7 the amount of the tertiary amine is larger than the upper limit defined in the claim. In Comparative Example 8 the amount of the organic halogen compound is smaller than the lower limit defined in the claim, while in Comparative Example 9 the amount of the tertiary amine is larger than the upper limit defined in the claim. When the amounts of the halogen compound and amine are smaller than the lower limits, curing by exposure to light becomes so worse that the attachability or detachability of the porcelain to or from the gypsum working model becomes inferior with a decrease in its shapeability. When they are larger than the upper limits, the modelling liquids assume a yellow tone before mixing with porcelains. Further, in an environment of 23° C., the reactivity of the modelling liquids with light is so high that when mixed with porcelains, they start to cure immediately and so cannot be used. In Comparative Example 5, the modelling liquid consists only of the photopolymerizable or polymerizable compound having at least one ethylenically unsaturated double bond and the organic solvent, and does not contain any component contributable to curing at all. Thus, this may be condensed with its low viscosity, but fails to give porcelains improved attachability to or detachability from the gypsum working model, and shapeability. In Comparative Examples 10 and 11, pure water having been most generally used in the art is used. In Comparative Example 10 no release agent is applied to the gypsum model, whereas in Comparative Example 11 Margin Separator made by Ishifuku Kinzoku Co., Ltd. is used as a separating material for the gypsum model. In Comparative Example 10, since the build up porcelain is prone to be deposited to the gypsum model, even experts can neither attach or detach it to or from the model nor shape it. In Comparative Example 11, some experts may carefully shape the porcelain by attaching or detaching it to or from the gypsum model, since the release agent is applied thereto, but will often fail. In any case, the modelling liquids are considerably different in refractive index form water (1.3327 at 23° C.). Consequently, it is impossible to make an previous estimate of what color tones the modelling liquids assume when mixed with GC Ceramibond M67 made by GC Toshi Kogyo Corporation. In Comparative Example 12, 1 part by weight of Plastodent (orange wax) made by Degussa Company is melted with a gas burner and mixed with 6 parts by weight of GC Ceramibond M67. It is utterly impossible to make a previous estimation of the color tone of the porcelain after sintered, since the orange tone of this wax is reflected. Moreover, since the wax is not condensed but produces much carbon, carbons can be produced to contaminate the inside of a porcelain furnace and may cause troubles to the furnace, when the porcelain is subjected to incineration. Besides, even when the wax is melted with a gas burner and incorporated into the porcelain, it solidifies immediately upon cooled down to room temperature due to its high crystallinity and so cannot be used. Therefore, the length of time allowed for dental operation is as short as 1-2 minutes, when the total amount of the porcelain is about 2 grams. The wax is thus very difficult to handle. In Comparative Example 13, SM Liquid made by Ducera Co., Ltd., is used. Designed to be heated and cured by hot air form a dryer, etc., this liquid is prone to be deposited to the gypsum model in the course of curing, so that its detachability from the gypsum model is much inferior. It is also utterly impossible to make a previous estimation what color tone this liquid assumes when mixed with GC Ceramibond M67 and sintered, since its refractive index (of 1.3381 at 23° C.) is very close to that of water. In Comparative Example 14, Spectrum Shoulder Porcelain VLC Medium made by Dentsply Co., Ltd. was used. Although having good curing properties, this liquid has a viscosity as high as 0.9799 Pa.s so that is cannot be condensed, making it impossible to remove its excessive portions. Therefore, black carbon remains after incineration and firing. Due to containing much catalysts such as photopolymerization initiators and reducing agents, the liquid itself assumes a yellow tone, and its is quite impossible to make a previous estimation what color it assumes when mixed with GC Ceramibond M67 and then fired.

The effects of the modelling liquid for dental porcelain according this invention will now be set out. (In order to prevent the metallic color of the cervical periphery of a metallic coping or frame from being seen through or exposed to view, porcelains are built up with the margin porcelain technique but without applying the metallic coping or frame to the cervical periphery)

1. After mixed with porcelain, the modelling liquid for dental porcelain according to this invention is built up on the cervical periphery and then exposed to light or reacts with the organic peroxide or pyrimidinetrione derivative and organometallic compound contained in the porcelain, or alternatively the organic solvent is volatilized off. The thus cured porcelain is temporarily bonded to the metallic coping or frame and so is easily removed from a gypsum working model. Thus, troublesome dental operations such as the building up and sintering of porcelains on a refractory model can be dispensed with. Consequently, the length of time allowed for dental operation can be much reduced with improvements in fitting accuracy.

2. Building up porcelain on a metallic coping or frame lined with a platinum foil is troublesome and timeconsuming, fails to obtain the cervical periphery in good condition, and incurs considerable expense due to the platinum foil being costly. The modelling liquid for dental porcelain according to this invention is much cheaper than the platinum foil, say, on the order of one tenth—a few tenths or one tenth—a few hundredths, thus leading to cost reductions.

3. When porcelains are condensed with water for its removal, as carried out conventionally, the form of the cervical periphery is so maintained only by wet bonding that it becomes out of shape even upon receiving a slight vibration or impact. Thus this cannot be applied to bridge work using a plurality of abutment teeth. Further, this method requires skill. After mixed with porcelains and built up in place, the modelling liquid for dental porcelain according to this invention is cured by exposure to light or reaction with the organic peroxide or pyrimidinetrione derivative and organometallic compound contained in the porcelain. Thus, the porcelain can be so easily removed from a gypsum working model that the form of the cervical periphery can be maintained to the end. This technique makes it possible to immediately remove the porcelain built up on the cervical periphery from the gypsum working model without any craftmanship, and so is easily applicable to bridge work using a plurality of abutment teeth. When porcelain is condensed with water for its removal, as carried out conventionally, it is required that a hydrophobic release material or surface curing agent be applied to the cervical periphery of the gypsum working model for easy removal of the condensed porcelain. Thus, the fitting of the porcelain to the cervical periphery gets worse relative to the thickness of the release material or surface curing material applied. After mixed with porcelains and built up in place, the modelling liquid for dental porcelain according to this invention is cured by exposure to light or reaction with the organic peroxide or pyrimidinetrione derivative and organometallic compound contained in the porcelain. Thus, the porcelain can be easily removed from the gypsum working model with no need of using such a hydrophobic release material or surface curing material. Consequently, the fitting of the the cervical periphery of the porcelain fired to a metal to the gypsum working model or even to the abutment teeth of a patient is much improved.

4. The modelling liquid for dental porcelain according to this invention shows a viscosity sufficient for condensation after mixed with porcelain and built up in place and before exposure to light or reaction with the organic peroxide or pyrimidinetrione derivative and organometallic compound contained in the porcelain. Thus, when the modelling liquid is in excess, it can be removed by tissue papers or gauzes. According to this invention, the organic material solid or semi-solid at normal temperature is diluted with an organic solvent. After building up, the porcelain is heated to a temperature higher than the boiling point of the organic solvent to volatilize the organic solvent alone, whereby the form of the porcelain can be maintained with a small amount of the wax residue. Subsequent incineration can further improve the fired porcelain because of the small amount of the wax residue. Thus, there is no fear that much carbon may be produced at the time of incineration to cause contamination, or breakdown of a furnace.

5. The modelling liquid for dental porcelains according to this invention is not to be cured by heat and the liquid wall not be softened by heat or not flow out by air pressure, thus the porcelain material will not be caused to flow out into the metallic coping or frame. Therefore, fitting of the porcelain to the gypsum model at the cervical periphery of the metallic coping or frame or even to the abutment teeth of a patient is much improved.

6. The modelling liquid for dental porcelain according to this invention can be well-condensed. Moreover, it can be sintered after removal of an excessive portion of the photopolymerizable or polymerizable compound having at least one ethylenically unsaturated double bond. When the photopolymerizable or polymerizable compound having at least one ethylenically unsaturated double bond has a high viscosity or the phototpolymerization reaction or the reaction with the organic peroxide or pyrimidinetrione and organometallic compound contained in the porcelain is very slow, the organic material solid or semi-solid at normal temperature and the photopolymerizable or polymerizable compound having at least one ethylenically unsaturated double bond are previously dissolved in an organic solvent having a high boiling point. After building up and condensating, the porcelain is heated to remove the aforesaid solvent. Since the remaining organic material solid or semi-solid at normal temperature solidifies, it is possible to maintain the form of the porcelain as built up.

(In order to obtain dental prostheses as close to natural teeth as possible, the special effects are added to porcelains with the use of internally or externally coloring porcelain materials).

1. The modelling liquid for dental porcelains according to this invention has a refractive index of 1.4–1.6 at 23° C., while porcelains have a refractive index of 1.47–1.50. This modelling liquid undergoes no substantial change in refractive index before and after exposure to light or the reaction with the organic peroxide or pyrimidinetrione derivative and organometallic compound contained in the porcelain, i.e., before and after curing. Thus, when some are selected from a number of internally or externally coloring porcelain materials to afford the desired special effect to the porcelain, thereby expressing sophisticated color tones, even novices can make a previous estimation of the color tone of the porcelain after firing. Therefore, it is possible to prevent such failures that porcelains are re-built up as often as is required in mixing with water, for the color tone of porcelain can be previously estimated. This renders it possible for anyone to achieve production of the special effects, which has so far been practiced by experts alone. The internally or externally coloring porcelain materials mixed with the modelling liquid according to this invention can be cured by exposure to light or reaction with the organic peroxide or pyrimidinetrione derivative and organometallic compound contained in the porcelain. This also makes it possible for anyone to build up or apply porcelain on the desired location at the desired thickness and to the desired extension. Moreover, the length of time needed for dental operation is one tenth to a few tenths of that required conventionally and the internally or externally coloring porcelain materials of the desired color tones can be selected precisely. Therefore, the special effects can be so easily imparted to porcelains that the prosthesis can be improved in the aesthetic appearance with improvements in quality and work efficiency.

2. The modelling liquid for dental porcelain according to this invention is designed to be built up by exposure to light or reaction with the organic peroxide or pyrimidinetrione and organometallic compound contained in the porcelain for its curing. Therefore, when such special effects as inner defects including cracking, yellowing, etc. or outer defects and insufficient calcification are produced to the porcelain, these can be done with use of a fine brush to cover such internal stains easily without any craftmanship. Consequently, it is possible to apply the special effects of constant quality to porcelains with internally or externally coloring porcelain materials at any desired time, since neither color mixing nor line thickening or blurring may take place, as is the case with mixing with water.

We claim:

1. A modeling liquid used for building up dental porcelain, comprising:
   (A) a photopolymerizable compound having at least one ethylenically unsaturated double bond,
   (B) a photopolymerizable initiator,
   (C) a reducing agent, and
   (D) a polymerization inhibitor, wherein said modelling liquid can be fired without effecting discoloration of a porcelain; and
   wherein said modeling liquid has a refractive index of 1.4 to 1.6 inclusive at 25° C. and a viscosity of 0.1 Pa.s or less at 23° C.

2. The modelling liquid of claim 1, further comprising an organic solvent.

3. The modelling liquid of claim 2, further comprising an organic material solid or semi-solid at room temperature.

4. The modelling liquid for dental porcelain as recited in claim 2, wherein said organic solvent is at least one solvent selected from the group consisting of hydrocarbons, halogenated hydrocarbons, alcohols, ethers/acetals, ketones, esters, polyhydric alcohols, derivatives of polyhydric alcohols, and nitrogen compounds.

5. The modelling liquid of claim 1, further comprising an organic material solid or semi-solid at room temperature.

6. The modelling liquid for dental porcelain as recited in claim 5, wherein said organic material solid or semi-solid at room temperature is at least one material selected from the group consisting of natural waxes, petroleum waxes, coal-based synthetic waxes, polyolefinic synthetic waxes, fat-based synthetic waxes, oil-based synthetic waxes, and alcoholic waxes having 13 or more carbon atoms.

7. The modelling liquid for dental porcelain as recited in claim 1, wherein said photopolymerizable or polymerizable compound having at least one ethylenically unsaturated double bond is a monofunctional methacrylate.

8. The modelling liquid for dental porcelain as recited in claim 1, wherein said photopolymerizable or polymerizable compound having at least one ethylenically unsaturated double bond is a polyfunctional methacrylate.

9. The modelling liquid for dental porcelain as recited in claim 1, wherein said photopolymerizable or polymerizable compound having at least one ethylenically unsaturated double bond is a monofunctional acrylate.

10. The modelling liquid for dental porcelain as recited in claim 1, wherein said photopolymerizable or polymerizable compound having at least one ethylenically unsaturated double bond is a polyfunctional acrylate.

11. The modelling liquid for dental porcelain as recited in claim 1, wherein said photopolymerization initiator is at least one initiator selected from the group consisting of alpha-diketone compounds, ketal compounds, anthraquinone compound, thioxanthone compounds, benzoin alkyl ether compounds and derivatives thereof.

12. The modelling liquid for dental porcelain as recited in claim 11, wherein said photopolymerization initiator is added in the range of 0.001 parts by weight inclusive to 15 parts by weight exclusive per 100 parts by weight of said photopolymerizable compound having at least one ethylenically unsaturated double bond.

13. The modelling liquid for dental porcelain as recited in claim 1, wherein said reducing agent is added in the range of 0.001 part by weight inclusive to 20 parts by weight exclusive per 100 parts by weight of said photopolymerizable compound having at least one ethylenically unsaturated double bond.

* * * * *